United States Patent
Quatieri et al.

(10) Patent No.: US 9,763,617 B2
(45) Date of Patent: Sep. 19, 2017

(54) PHONOLOGICALLY-BASED BIOMARKERS FOR MAJOR DEPRESSIVE DISORDER

(75) Inventors: Thomas Francis Quatieri, Newtonville, MA (US); Nicolas Malyska, Watertown, MA (US); Andrea Carolina Trevino, Urbana, IL (US)

(73) Assignee: Massachusetts Institute of Technology, Cambridge, MA (US)

( * ) Notice: Subject to any disclaimer, the term of this patent is extended or adjusted under 35 U.S.C. 154(b) by 850 days.

(21) Appl. No.: 13/561,458

(22) Filed: Jul. 30, 2012

(65) Prior Publication Data

US 2013/0090927 A1 Apr. 11, 2013

Related U.S. Application Data

(60) Provisional application No. 61/514,371, filed on Aug. 2, 2011.

(51) Int. Cl.
| | | |
|---|---|---|
| *G10L 25/63* | (2013.01) | |
| *A61B 5/00* | (2006.01) | |
| *G10L 15/04* | (2013.01) | |
| *G10L 25/90* | (2013.01) | |
| *G10L 25/18* | (2013.01) | |

(Continued)

(52) U.S. Cl.
CPC ............ *A61B 5/4803* (2013.01); *A61B 5/165* (2013.01); *G10L 15/04* (2013.01); *G10L 25/06* (2013.01); *G10L 25/18* (2013.01); *G10L 25/21* (2013.01); *G10L 25/66* (2013.01); *G10L 25/90* (2013.01);

(Continued)

(58) Field of Classification Search
CPC ......... G10L 25/63; G10L 25/66; G10L 15/04; G10L 25/06; G10L 25/18; G10L 25/21; G10L 25/90; G10L 17/26; G10L 15/02; G10L 15/00; G10L 15/063; G10L 15/14; G10L 17/16; G10L 2015/0631; G10L 25/03; G10L 15/06; G10L 17/00; G10L 13/08; G10L 15/075

See application file for complete search history.

(56) References Cited

U.S. PATENT DOCUMENTS

| | | | | |
|---|---|---|---|---|
| 2002/0111794 A1* | 8/2002 | Yamamoto | .............. | G10L 13/08 704/200 |
| 2004/0019484 A1* | 1/2004 | Kobayashi | .............. | G10L 13/02 704/258 |

(Continued)

FOREIGN PATENT DOCUMENTS

WO WO 2015/102733 7/2015

OTHER PUBLICATIONS

Wu, et al., Emotion Recognition from Speech Using IG-Based Feature Compensation, The Association for computational Linguistics and Chinese Language Processing, Oct. 10, 2006, pp. 65-78.*

(Continued)

*Primary Examiner* — Abdelali Serrou
(74) *Attorney, Agent, or Firm* — Occhiuti & Rohlicek LLP

(57) ABSTRACT

A system and a method for assessing a condition in a subject. Phones from speech of the subject are recognized, one or more prosodic or speech-excitation-source features of the phones are extracted, and an assessment of a condition of the subject, is generated based on a correlation between the features of the phones and the condition.

35 Claims, 17 Drawing Sheets
(7 of 17 Drawing Sheet(s) Filed in Color)

(51) Int. Cl.
  G10L 25/21   (2013.01)
  G10L 25/06   (2013.01)
  G10L 25/66   (2013.01)
  A61B 5/16    (2006.01)
  G10L 15/02   (2006.01)
(52) U.S. Cl.
  CPC ....... A61B 5/7267 (2013.01); G10L 2015/025 (2013.01)

(56) References Cited

U.S. PATENT DOCUMENTS

| | | | | |
|---|---|---|---|---|
| 2004/0062364 | A1* | 4/2004 | Dezonno et al. | 379/88.14 |
| 2006/0069559 | A1* | 3/2006 | Ariyoshi | G10L 19/0018 704/246 |
| 2009/0191521 | A1* | 7/2009 | Paul | G10L 17/16 434/169 |
| 2009/0208913 | A1* | 8/2009 | Xu | A61B 5/7264 434/169 |
| 2009/0313019 | A1* | 12/2009 | Kato | G10L 17/26 704/254 |
| 2010/0235451 | A1* | 9/2010 | Yu | G06F 15/16 709/206 |
| 2011/0141258 | A1* | 6/2011 | Song et al. | 348/77 |
| 2012/0209606 | A1* | 8/2012 | Gorodetsky et al. | 704/235 |
| 2013/0166291 | A1 | 6/2013 | Lech et al. | |
| 2015/0112232 | A1 | 4/2015 | Quatieri et al. | |

OTHER PUBLICATIONS

Metz, et al. Fusion of Acoustic and Linguistic Speech Features for Emotion Detection, 2009 IEEE International Conference on Semantic Computing, Jun. 2009, pp. 153-160.*

Bagby, R. M., A. G. Ryder, M.A., D. R. Schuller, and M. B. Marshall, "The Hamilton Depression Rating Scale: Has the Gold Standard Become a Lead Weight?", *Am J Psychiatry* 161: 2163-2177 (Dec. 2004).

Cannizzaro, M., B. Harel, et al. (2004)."Voice acoustical measurement of the severity of major depression." *Brain and cognition* 56(1): 30-35.

Cohn, J., T. Kruez, et al., "Detecting depression from facial actions and vocal prosody." 3rd International Conference on Affective Computing and Intelligent Interaction and Workshops (Sep. 10-12, 2009).

Schuller, Björn, et al. (2009), "The Interspeech 2009 Emotion Challenge," in Interspeech-2009, pp. 312-315.

Fava, M. and K. Kendler (2000). "Major depressive disorder." *Neuron* 28(2): 335-341.

Flint, A., S. Black, et al. (1993). "Abnormal speech articulation, psychomotor retardation, and subcortical dysfunction in major depression." *Journal of psychiatric research* 27(3): 309-319.

France, D., R. Shiavi, et al. (2000). "Acoustical properties of speech as indicators of depression and suicidal risk." *IEEE Transactions on Biomedical Engineering* 47(7): 829.

Hamilton, M. (1960). "A rating scale for depression." *J. Neurol. Neurosurg. Psychiat.*, 23(1): 56.

Lemke, M., P. Puhl, et al. (1999). "Psychomotor retardation and anhedonia in depression." *Acta Psychiatrica Scandinavica* 99(4): 252-256.

Kukolich, L., and Lippman, R., LNKnet User's Guide, MIT Lincoln Laboratory (Feb. 2004).

Low, L.A., Maddage, Lech, M., Sheeber, L., Allen, N. (2010). "Influence of acoustic low-level descriptors in the detection of clinical depression in adults," *Proceedings of the 2010 IEEE International Conference on Acoustics, Speech and Signal Processing.*

Moore, E., M. Clements, et al. (2008). "Critical analysis of the impact of glottal features in the classification of clinical depression in speech." *IEEE Transactions on Biomedical Engineering* 55(1): 96-107.

Moore II, E., M. Clements, et al. (2003). "Analysis of prosodic variation in speech for clinical depression." *Proceedings of the 25th Annual International Conference of the IEEE EMBS*: 2925-2928.

Mundt, J., P. Snyder, et al. (2007). "Voice acoustic measures of depression severity and treatment response collected via interactive voice response (IVR) technology." *Journal of Neurolinguistics* 20(1): 50-64.

Ozdas, A., R. Shiavi, et al. (2004). "Investigation of vocal jitter and glottal flow spectrum as possible cues for depression and near-term suicidal risk." *IEEE Transactions on Biomedical Engineering* 51(9): 1530-1540.

Ozdas, A., R. Shiavi, et al. (2004). "Analysis of vocal tract characteristics for near-term suicidal risk assessment." *Methods Inf Med.* 43(1):36-8.

Pittam, J., (1993) "Vocal Expression and Communication of Emotion." In *Handbook of Emotions*, Michael Lewis, ed. (NY: Guilford Publications) pp. 185-197.

Quatieri, T.F., *Discrete-Time Speech Signal Processing: Principles and Practice*, (title page and table of contents) Faye Gemmellaro, ed. (NJ: Prentice Hall PTR) (2001).

Rouas J., "Automatic Prosodic Variations Modeling for Language and Dialect Discrimination," *IEEE Trans. Audio, Speech, and Language Proc.*, 15(6): 1904-1911 (Aug. 2007).

Rouas J., Farinas J., Pellegrino F., André-Obrech R., "Rhythmic unit extraction and modeling for automatic language identification," *Speech Communication* 47 (2005) 436-456.

Shen, W., White. C, Hazen, T.J., "A comparison of query-by-example methods for spoken term detection," in Interspeech-2009, pp. 2143-2146.

Sobin, C. and H. Sackeim (1997). "Psychomotor symptoms of depression." *American Journal of Psychiatry* 154(1): 4-17.

World Health Organization (2001). *The World Health Report : 2001 : Mental health : new understanding, new hope.* Geneva, World Health Organization.

Van Heerden, C.J., and Bernard, E., "Speaker-specific variability of Phoneme Durations," Paper, (2008).

Van Heerden, C.J., "Phoneme Duration Modelling for Speaker Verification," master's thesis, University of Pretoria (Apr. 2008).

Sapir, S., et al., "Formant Centralization Ratio: A Proposal for a New Acoustic Measure of Dysarthric Speech," *Journal of Speech, Language, and Hearing Research*, 53: 114-125 (Feb. 2010).

James R. Williamson, et al., "Vocal biomarkers of depression based on motor incoordination", Proceedings of the 3rd ACM International Workshop on Audio/Visual Emotion Challenge, AVEC '13, Oct. 21, 2013 (Oct. 21, 2013), pp. 41-48, XP55194796, New York, New York, USA, DOI: 10.1145/2512530.2512531, ISBN 978-1-45-032395-6.

J.R. Williamson, D.W. Bliss; D.W. Browne; J.T. Narayanan, "Seizure prediction using EEG spatiotemporal correlation structure", Epilepsy & Behavior, vol. 25, No. 2, 2012, pp. 230-238, XP002740764, cited in the application the whole document.

Brian S. Helfer, et al., "Classification of depression state based on articulatory precision", Aug. 2013 (Aug. 2013), XP055194854, Retrieved from the Internet: URL:http://citeseerx.ist.psu.edu/viewdoc/download?doi=10.1.1.361.2870&rep=repl&type=pdf [retrieved on Jun. 10, 2015] the whole document.

Yaozhang Pan et al., "Seizure detection based on spatiotemporal correlation and frequency regularity of scalp EEG", 2012 International Joint Conference on Neural Networks (IJCNN 2012—Brisbane) IEEE Piscataway, NJ, USA, 2012, p. 7 pp. XP002740765, ISBN: 978-1-4673-1488-6 the whole document.

Douglas Sturim et al., "Automatic Detection of Depression in Speech using Gaussian Mixture Modeling with Factor Analysis", 2001, XP055194860, Retrieved from the Internet: URL:https://wn1.11.mit.cdu/mission/cybersec/publications/publication-files/full_papers/2011_06_28 SturimD_Interspeech_FP.pdf.pdf [retrieved on Jun. 10, 2015] the whole document.

* cited by examiner

Table I

| Rate Measure | Score Category | Spearman Correlation | p-value |
|---|---|---|---|
| Speaking - Phone Rate | HAMD Work and Activities | -0.20 | 0.01<p<0.05 |
| | HAMD Pyschomotor Retardation | -0.38 | p = 3.6e-5 |
| | HAMD TOTAL | -0.22 | 0.01<p<0.05 |
| Articulation - Phone Rate | HAMD Pyschomotor Retardation | -0.46 | p = 3.2e-7 |
| | HAMD Weight Loss | -0.19 | 0.01<p<0.05 |

Boxed entries indicate cases of high significance with $p < 0.01$.

FIG. 3

Table II

| Measure | Score Category | Spearman Correlation | p-value |
|---|---|---|---|
| Pause Length | HAMD Mood | 0.28 | p = 0.003 |
| | HAMD Guilt | 0.20 | 0.01<p<0.05 |
| | HAMD Suicide | 0.27 | p = 0.004 |
| | HAMD Work and Activities | 0.28 | p = 0.002 |
| | HAMD Psychomotor Retardation | 0.33 | p = 0.0003 |
| | HAMD Anxiety Psychic | 0.24 | p = 0.009 |
| | HAMD Hypochondriasis | 0.26 | p = 0.005 |
| | HAMD TOTAL | 0.26 | p = 0.005 |
| Ratio of Pause Time | HAMD Guilt | 0.21 | 0.01<p<0.05 |
| | HAMD Insomnia Early Morning | 0.20 | 0.01<p<0.05 |
| | HAMD Work and Activities | 0.19 | 0.01<p<0.05 |
| | HAMD Anxiety Psychic | 0.24 | 0.01<p<0.05 |
| | HAMD TOTAL | 0.25 | p = 0.009 |

Pauses are identified by the phone recognizer; the average of all durations per session is used as the feature. Boxed entries indicate cases of high significance with $p < 0.01$.

FIG. 4

Table III

| Phones used | Score Category | Spearman Correlation | p-value |
|---|---|---|---|
| (sil, aa, g, jh, k, ng, s, t) | HAMD Mood | 0.43 | p = 2.7e-6 |
| (uh, b, jh, n, p, t, z) | HAMD Insomnia Middle of the Night | 0.37 | p = 6.8e-5 |
| (sil, aa, ih, ow, eh, s) | HAMD Work and Activities | 0.39 | p = 2.7e-5 |
| (sil, ae, iy, ay, ey, ao, ow, eh, aw, uh, er, g, k, ng, r, s, t, v, w, z) | HAMD Psychomotor Retardation | 0.58 | p = 1.7e-11 |
| (aw, jh, p, t) | HAMD Agitation | 0.34 | p = 2.0e-4 |
| (aa, uw, uh, b) | HAMD General Symptoms | 0.40 | p = 1.4e-5 |
| (aa, ao, s, w) | HAMD Genital Symptoms | 0.42 | p = 4.5e-6 |
| (sil, ao, g, n, ng, s) | HAMD Hypochondriasis | 0.39 | p = 2.0e-5 |
| (iy, ey, ih, eh, f, l, v) | HAMD Weight Loss | 0.39 | p = 2.6e-5 |
| (sil, s, k, ih, aa) | HAMD TOTAL | 0.35 | p = 1.8e-4 |

FIG. 7

PHONOLOGICALLY-BASED BIOMARKERS FOR MAJOR DEPRESSIVE DISORDER

RELATED APPLICATION

This application claims the benefit of U.S. Provisional Application No. 61/514,371, filed on Aug. 2, 2011.

The entire teachings of the above application are incorporated herein by reference.

GOVERNMENT SUPPORT

This invention was made with government support under Air Force Contract FA8721-05-C-0002 awarded by the Department of Defense. The government has certain rights in the invention.

BACKGROUND OF THE INVENTION

Major Depressive Disorder (MDD) places a staggering global burden on society. Of all mental disorders, MDD accounts for 4.4% of the total disability-adjusted life years (DALYs) lost and accounts for 11.9% of total years lost due to disability (YLD). With current trends, projection for the year 2020 is that depression will be second only to ischemic heart disease as the cause of DALYs lost worldwide.

A standard method of evaluating levels of MDD in patients is the clinical 17-question "Hamilton-D" or "HAMD" assessment that results in a total score of the patient, which is then translated into a clinical assessment by a physician. To determine the overall or total score, individual ratings are first determined for symptom sub-topics (such as mood, guilt, psychomotor retardation, suicidal tendency, etc.); the total score is the aggregate of the ratings for all sub-topics. Although the HAMD assessment is a standard evaluation method, there are well-known concerns about its validity and reliability.

SUMMARY OF THE INVENTION

The questions concerning HAMD score validity notwithstanding, accurate diagnosis of MDD requires intensive training and experience. Accordingly, there is a need for an automatic means to help detect and/or monitor depression.

In one example embodiment, the present invention is a method of assessing a condition in a subject. The method comprises recognizing phones from speech of the subject; extracting one or more prosodic or speech-excitation-source features of the phones from the speech of the subject; and generating an assessment of a condition of the subject, based on a correlation between the one or more features of the phones and the condition.

In another example embodiment, the present invention is a method of detecting a correlation between a condition and a feature in speech of a subject. The method comprises recognizing phones from speech of one or more subjects; extracting one or more prosodic or speech-excitation-source features of the phones from the speech of the one or more subjects, at least one subject having a condition; and determining a correlation between the one or more features of the phones and the condition.

In another example embodiment, the present invention is a system for assessing a condition in a subject. The system comprises a phone recognizer that recognizes phones from speech of the subject; a feature extractor that extracts one or more prosodic or speech-excitation-source features of the phones from speech of the subject; and an assessment generator that generates an assessment of a condition in the subject based on a correlation between the one or more features of the phones extracted from speech of the subject and the condition.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 3 is Table I, which shows score correlations with Speaking and Articulation rate.

FIG. 4 is Table II, which shows Score correlations with Pause Features.

FIG. 7 is Table III, which shows Score correlations with Signed Aggregate Phone length.

DETAILED DESCRIPTION OF THE INVENTION

Figure 1:
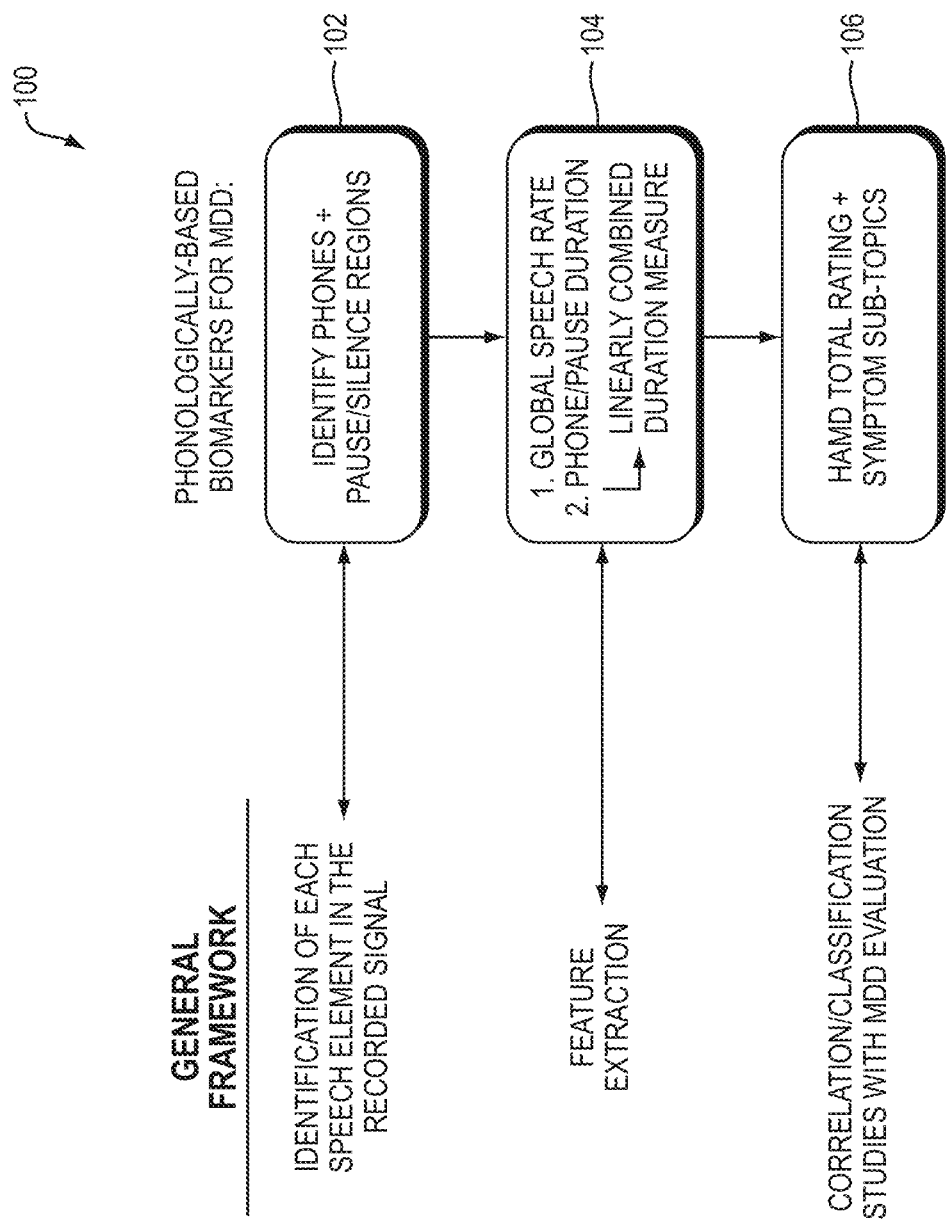
FIG. 1 is an illustration of an algorithm employed by an example embodiment of the present invention.

A description of example embodiments of the invention follows.

As used herein, the term "phoneme" means "the smallest structural unit that distinguishes meaning in a language."

As used herein, the term "phone" means "an instance of a phoneme in the actual utterances."

As used herein, the term "biomarker" means a naturally occurring characteristic by which a condition, a process or a state, e.g. disease, can be identified.

As used herein, a "subject" includes mammals, e.g., humans, companion animals (e.g., dogs, cats, birds, aquarium fish and the like), farm animals (e.g., cows, sheep, pigs, horses, fowl, farm-raised fish and the like) and laboratory animals (e.g., rats, mice, guinea pigs, birds, aquarium fish and the like). In a preferred embodiment of the disclosed methods, the subject is human.

As used herein, a "condition" includes any normal or pathological medical, physiological, emotional, neural, psychological, or physical process or state in a subject that can be identified by a biomarker. Examples include, but are not limited to stress, traumatic brain injury, post-traumatic stress disorder, Parkinson's disease, Aphasia, Autism, Alzeimer's disease, stroke, sleep disorders, including chronic, anxiety disorders, multiple sclerosis, cerebral palsy, and major depressive disorder (MDD). Additionally, the term "condition" includes heat/cold exposure effects, effects of sleep deprivation, effects of fatigue and various emotional states such as anger, sadness, or joy.

A "measure" of a condition is a measurable, e.g. quantifiable, value by which a condition can be predicted, diagnosed, or monitored by a clinician. Examples of measures include clinical scores, such as HAMD or directly observable physical values such as blood pressure, skin conductance, pulse rate, among others.

Currently, the most widely used measure used to identify MDD is the subject's HAMD total score. One class of biomarkers of growing interest is the large group of vocal features that have been observed to change with a patient's mental condition and emotional state. Examples include vocal characteristics of prosody (e.g., pitch and speech rate), spectral features, and glottal (vocal fold) excitation patterns. It has now been discovered that certain features of the phones in a subject's speech significantly separate control and depressed patient groups. Specifically, it has now been discovered that depression severity can be derived from phonologically-based measures of speech rate. Additionally it has been discovered that phonologically-based measures of speech rate also correlates with symptom-specific components that comprise the standard 17-item HAMD composite assessment of depression. For example, high correlations have been discovered between a subset of individual phone durations and the HAMD Psychomotor Retardation subscore.

As used herein, the term "derivative" means "derivative with respect to time."

"A feature of the phones" or "a phone-based feature" include, but are not limited to any one or more of the following examples:

Duration, including absolute duration of a phone or a time derivative of duration of a phone, computed by measuring the relative change between feature values on consecutive session days for each subject.

Energy, including absolute energy of a phone or energy variance or a phone, variance of energy derivative; energy variance out of each output of a filter-bank. As used herein, a "filter-bank" is a bank of bandpass filters spread along the frequency axis, thus doing a frequency-based decomposition; energy derivatives of filter-bank outputs; variance of energy derivatives of filter-bank outputs. The energy of the phone can be measured, for example, by using sum of squared waveform values over a time window (approximately 25 ms) divided by the window length. The window slides at a 10 ms frame interval. The window can also be the duration of a phone. This approach can be used on the original speech or frequency-decomposed versions via a filter bank.

Pitch of a phone, including absolute pitch, pitch variance; pitch derivative; variance of pitch derivative.

Aspiration (breathiness) of a phone measured as energy of a phone in question relative to other phones or as noise turbulence created at the vocal cords, as well as variance, derivative, and variance of derivative thereof.

Glottal flow of a phone, measured as air flow through vocal folds. Shimmer, jitter, and pulse-event patterns computed from these air-flow estimates may also be calculated.

Frequency-dependent energy of a phone, measured as amplitude of the modulation of a given wave band obtained by frequency decomposition of a phone.

Additionally, all of the above features may be further subjected to modulation analysis to derive more features. For example, frequency decomposition of time-dependencies of each feature can be obtained.

As used herein, "a phone-dependent prosodic feature" is any characteristic of speech that provides information about the timing, intonation, and/or energy (including relationships between these elements or quantities derived from these elements) for a given phone type. Examples of timing features include the duration, start time, end time, and derived values and statistics. Examples of intonation features include fundamental frequency, pitch, and derived values and statistics. Examples of energy features include amplitude, RMS power, mean-squared energy, and derived values and statistics.

As used herein, "a speech-excitation-source feature" refers to any value relating to the mechanical, acoustical, or aero-acoustic vibrations/movements in the vicinity of the larynx, glottis, vocal folds, false-vocal folds, pharynx, and other related tissues that provide excitation for the speech-production system. In the classic source-filter model, the speech-excitation source is the signal which is input into a model of the vocal-tract tubes.

Accordingly, in an example embodiment, the present invention is a method of assessing a condition in a subject. The method comprises recognizing phones from speech of the subject; extracting one or more prosodic or speech-excitation-source features of the phones from the speech of the subject; and generating an assessment of a condition of the subject, based on a correlation between the one or more features of the phones and the condition. For example, the condition has a measure and the correlation is between the measure and the one or more features of the phones. Examples of the conditions include, but are not limited to, traumatic brain injury, post-traumatic stress disorder, Parkinson's disease, Aphasia, Autism, Alzheimer's disease, stroke, sleep disorders, including chronic, anxiety disorders, multiple sclerosis, cerebral palsy, and major depressive disorder (MDD). Examples of the features of the phones include, but are not limited to, duration of phones, energy of phones, pitch of phones, aspiration of phones, glottal flow of phones or frequency-dependent energy of phones.

In example embodiments, the phones are recognized automatically. In other example embodiments, the speech of the subject is a running speech, e.g. conversational speech or a read sentence.

In an example embodiment, the method further includes computing an average duration of the one or more phones in speech of the subject.

In an example embodiment, the feature of the phones is a phone-duration-based speech rate of the subject, the condition is MDD, and the measure is the psychomotor retardation sub-score of the Hamilton-D score. The phone-duration-based speech rate of the subject can be determined by various methods. For example, the phone-duration-based speech rate of the subject can be determined by taking a reciprocal of the average duration of the one or more phones in speech of the subject. Alternatively, the phone-duration-based speech rate of the subject can be determined by averaging the reciprocals of the duration of phones in the subject speech. Other ways of determining the phone-duration-based speech rate of the subject can be devised by a person of ordinary skill.

For example, the condition can be a Major Depressive Disorder and the measure is a Hamilton-D score or a subscore thereof; the feature of the phones can be duration of the phones; the method can further include computing average duration of the phones in speech of the subject; and generating the assessment of the condition can include computing a weighted sum of the average duration of the phones, wherein the weights correspond to correlation coefficients between the average duration of the phones and the Hamilton-D score or a subscore thereof. In certain example embodiment, the method further includes generating an estimate of the Hamilton-D score of the subject or a subscore thereof and displaying the estimate of the Hamilton-D score of the subject or a subscore thereof.

In an example embodiment, the present invention is a method of detecting a correlation between a condition and a feature in speech of a subject. The method comprises recognizing phones from speech of one or more subjects; extracting one or more features of the phones from the speech of the one or more subjects, at least one subject having a condition; and determining a correlation between the one or more features of the phones and the condition. For example, the condition has a measure and the correlation is between the measure and the one or more features of the phones. In an example embodiment, the features of the phones include duration of the phones in the speech of the one or more subjects. The method can further include computing average duration of the one or more phones in the speech of the one or more subjects.

For example, the condition can be a Major Depressive Disorder and the measure is a Hamilton-D score or a subscore thereof; the feature of the phones can be the duration of the phones; the method can further include computing average duration of the phones; and determining the correlation can include computing, for each subject, correlation coefficients between the average duration of the phones and the Hamilton-D score or a subscore thereof.

In an example embodiment, the present invention is a system for assessing a condition in a subject. The system comprises a phone recognizer that recognizes phones from speech of the subject; a feature extractor that extracts one or more prosodic or speech-excitation-source features of the phones from the speech of the subject; and an assessment generator that generates an assessment of a condition having a biomarker in the subject based on a correlation between the one or more features of the phones and the condition. In example embodiments, the system further includes a display. For example, the assessment generator can further generate an estimate of the Hamilton-D score of the subject or a subscore thereof and the display can display the estimate of the Hamilton-D score of the subject or a subscore thereof.

The methods and systems disclosed herein can be used as non-invasive clinical tool, for example for remote assessment of a condition as well as for detection of emotional states of a subject.

The methods and systems of the present invention can employ either an estimation algorithms or a classification algorithm to generate an assessment of a condition. Any known estimation or classification algorithm can be employed.

As used herein, "estimation" is a process of deriving a value (or a measure) related to a condition from a set of phone-dependent features. As used herein, "classification" is a process of assigning a condition to one out of a plurality of possible discrete categories based on a set of phone-dependent features. Classification for major depressive disorder, for example, might involve categorizing a person as exhibiting clinical depression (category 1) or not exhibiting clinical depression (category 2).

Any of estimation approaches known to a person of ordinary skill in the art can be employed by the example embodiments of the system and methods described herein. Examples include:
  weighing phone-dependent features in test utterance by set of values derived from correlations between phone-dependent features and a condition and summing these weighted values; the weights can optionally be normalized;
  employing Pearson correlation and testing for a linear relationship between the phone-derived features and a measure of a condition;
  employing Spearman correlation and testing for a monotonic relationship between the phone-derived features and a measure of a condition.

Further examples of algorithms suitable for estimation include: minimum mean squared error estimation (MMSE); Bayes least squared error estimation (BLSE); Maximum-likelihood estimation; Maximum a posteriori (MAP) estimation; Bayes estimation; linear classifiers; Fisher's linear discriminant; employing logistic regression; Naive Bayes classifier; Perceptron (a single layer, neural-net classifier which takes features as input and outputs a classification); support vector machines (SVM); least squares support vector machines; quadratic classifiers; kernel estimation; K-nearest neighbor; boosting; decision trees; neural networks; Bayesian networks; and vector quantization.

EXEMPLIFICATION

Example 1: HAMD Correlates with Phonologically-Based Biomarkers

The correlations between phonologically-based biomarkers and the clinical HAMD severity ratings, was investigated for a 35-speaker free-response speech database reported in Mundt, Snyder, et al. (2007). "Voice acoustic measures of depression severity and treatment response collected via interactive voice response (IVR) technology." Journal of Neurolinguistics 20(1): 50-64. Global speech rate measures were computed and the correlations of phonologically-based biomarkers with the HAMD total and sub-topic ratings were shown. Using a simple Gaussian-likelihood classifier, the accuracy in classifying the individual symptom HAMD sub-topic ratings was demonstrated by a multi-class classifier where each rating level is set as its own class. The classification root mean squared error (RMSE) was used as a measure of accuracy.

These global rate measures were computed by finding the average phone rate using an automatic phone recognition algorithm. The correlations of the HAMD ratings with the average duration of pauses and automatic recognition-based individual English phone durations were then examined, providing a fine-grained analysis of speech timing.

The individual phone durations that showed significant correlations within a single HAMD category (total or sub-topic) were observed to cluster approximately within manner-of-articulation categories and according to the strength of intercorrelation between sub-topics.

As an extension of the individual phone duration results, the energy spread of a phone was used as an alternate duration measure; the energy spread measure revealed some similar phone-specific correlation patterns and more changes in correlations with burst consonants relative to those calculated from the recognition-based duration. A broad overview of the methods employed herein is illustrated in FIG. 1. As shown in FIG. 1, method 100 includes step 102 in which phones are identified, step 104, in which phone duration is measured, and step 106, in which HAMD score os its subscore are generated, based on the duration of phones.

Major Depressive Disorder (MDD) is characterized by one or more Major Depressive Episodes (MDE), where an MDE is defined as a period of at least two weeks during which either a depressed mood dominates or markedly diminished interest, also known as anhedonia, is observed. Along with this, the American Psychiatric Association standard recommends that at least four or more of the following symptoms also be present for diagnosis: significant change in weight or appetite, insomnia or hypersomnia nearly every day, psychomotor agitation or retardation (clearly observable by others), fatigue, feelings of worthlessness or excessive guilt, diminished ability to concentrate or decide, and/or recurrent thoughts of death or suicide. These standards are reflected in the HAMD score, which encompasses multiple symptoms in order to gauge the overall severity of depressive state.

The standard method of evaluating levels of MDD in patients is the clinical 17-question HAMD assessment. To determine the overall or total score, individual or sub-scores ratings are first determined for symptom sub-topics (such as mood, guilt, psychomotor retardation, suicidal tendency, etc.); the total score is the aggregate of the sub-scores for all sub-topics. The sub-topic component list for the HAMD (17 symptom sub-topics) evaluation is well known to a clinician of ordinary skill in the art of MDD. Scores for component sub-topics have ranges of (0-2), (0-3), or (0-4).

The data used in this analysis was collected by Mundt et al., mentioned above. Thirty-five physician-referred subjects (20 women and 15 men, mean age 41.8 years) participated in this study. The subjects were predominately Caucasian (88.6%), with four subjects of other descent. The subjects had all recently started on pharmacotherapy and/or psychotherapy for depression and continued treatment over a 6-week assessment period. Speech recordings (sampled at 8 kHz) were collected at weeks 0, 2, 4, and 6 during an interview and assessment process that involved HAMD scoring. To avoid telephone-channel effects, only the samples of conversational (free-response) speech recorded in the clinic were used in this work. Additionally, only data from subjects who completed the entire longitudinal study was used. This resulted in approximately 3-6 minutes of speech per session (i.e., per day).

Ratings from the 17-item HAMD clinical MDD evaluation were chosen as comparison points in our study. Individual sub-topic ratings from each evaluation were also used both in our correlation studies and classification-algorithm development.

Figure 2:
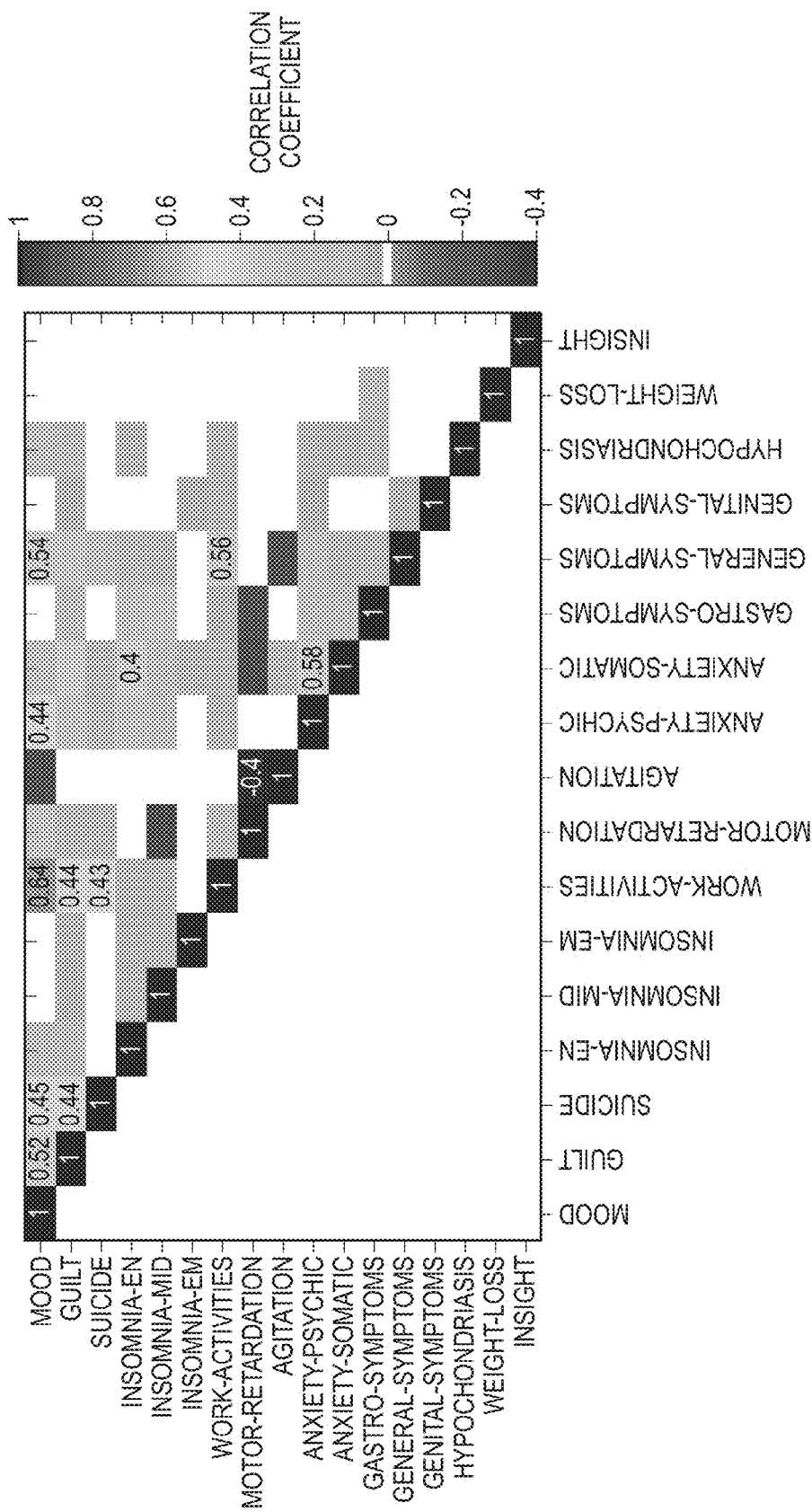
FIG. 2 is a table of HAMD sub-topic intercorrelations; only significant (p-values<0.05) correlations are shown with non-zero magnitude. All correlations values greater than 0.4 in absolute value are listed in the table. For clarity, all values below the diagonal of the symmetric correlation matrix have been omitted.

An important additional consideration is the intercorrelations between the HAMD symptom sub-topics. FIG. 2 shows all significant intercorrelations between the HAMD sub-topics, computed with our dataset. The greatest absolute correlation of 0.64 corresponds to the Mood and Work-Activities sub-topics. High significant correlations group the sub-topics of Mood, Guilt, Suicide, and Work-Activities together. Relevant to the findings in this work, the Psychomotor Retardation sub-topic has the strongest correlations with Agitation (−0.40) and Mood (0.36, not labeled).

The present work is based on the hypothesis that general psychomotor slowing manifests itself in the speech rate, motivated by observed psychomotor symptoms of depression. Here, a measure of speech rate derived from the durations of individual phones was investigated. For the phone-based rate measurements, a phone recognition algorithm based on a Hidden Markov Model approach was used, as described in greater detail in Shen, White, Hazen, "A comparison of query-by-example methods for spoken term detection," ICASSP10, the relevant teachings of which are incorporated herein by reference.

The number of speech units per second over the entire duration of a single patient's free-response session was computed. As used herein, the term "speaking rate" refers to the phone rate over the total session time, with times when the speech is not active (pauses) included in the total session time. This is in contrast to the term "articulation rate," which is computed as the phone rate over only the time during which speech is active.

Phone rates were computed for each individual subject and session day using the database described in Mundt et. al. Correlations between these global rate measures and the total HAMD score, along with its sub-scores (17 individual symptom sub-topics), were all computed. Results were processed using Spearman correlation due to the quantized ranking nature of the HAMD depression scores and the possible non-linear relationship between score and speech feature. Thus, the correlation results determined if a monotonic relationship exists between extracted speech features and depression-rating scores. Results are shown in FIG. 3, which presents Table 1.

Different categories of significance of a correlation are given by p-values: $p<0.01$ highly significant; $p<0.05$ significant; $p>0.05$ not significant. All significant correlations of phone rate with depression ratings are shown in Table I (FIG. 3). Examining the HAMD total score, a significant correlation is detected between this total and phone-based speaking rate. The articulation rate measure did not show the same correlation with HAMD total, but did show a stronger relationship with the Psychomotor Retardation rating than the more general speaking rate. The most significant correlations for both speaking and articulation rate measures was seen with the Psychomotor Retardation ratings.

The use of an automatic method of phone recognition allowed the methods and systems described herein to analyze much longer samples of speech than previously reported and thus obtain a more reliable estimate.

As discussed below, the speech signal was decomposed into individual phones and the phone-specific relationships with depression severity were analyzed. Distinct relationships between phone-specific duration and the severity of certain symptoms were demonstrated. Two different definitions of phone duration are used herein: 1) phone boundaries via an automatic phone recognizer and 2) width of the energy spread around the centroid of a signal within defined phone boundaries. Decomposition into phone-specific measures allows for a more refined analysis of speech timing. As above, due to the quantized nature of the rankings, Spearman correlation was used to determine if a monotonic relationship exists between extracted speech features and depression-rating scores.

Using an automatic phone recognition algorithm, the individual phones and their durations were detected. The silence or "pause" regions within a free-response speech session were first examined.

As used herein, the term "phone length" is the duration of consonants and vowels. "Phone length," in contrast to pause length, varied in a non-uniform manner over the observed depression severities. Specifically, the severity of each symptom sub-topic score exhibited different corresponding phone length correlation patterns over all of our recognition-defined phones.

The automatic phone recognition algorithm categorizes pauses as distinct speech units, with lengths determined by estimated boundaries. Both average pause length and percent total pause time were examined and the results are summarized in FIG. 4, which presents Table II.

The correlations between the average pause length over a single speech session and the HAMD total and corresponding sub-topic ratings were computed; the results are shown in FIG. 4 (Table II). The average pause length is inversely related to the overall speaking rate and so the HAMD Psychomotor Retardation score again shows the highest correlation value. The HAMD total score, along with a large number of sub-topics, show a significant worsening of condition with longer average pause length. The ratio of pause time measure is defined as the percent of total pause time relative to the total time of the free-response speech session. This feature, in contrast to the average pause length measure, is more sensitive to a difference in the amount of time spent in a pause period, relative to the time in active speech. Thus, a change in time spent thinking, deciding, or delaying further active speech would be captured by the ratio of pause time measure. For this ratio, a highly significant correlation was seen with only the HAMD total score. Most of the significant correlations with total and sub-topic symptom scores seen with ratio of pause time were also correlated with average pause length; the only sub-topic that does not follow this rule is the HAMD measure of Early Morning Insomnia, which shows a higher pause ratio with worsening of condition.

Figure 5:
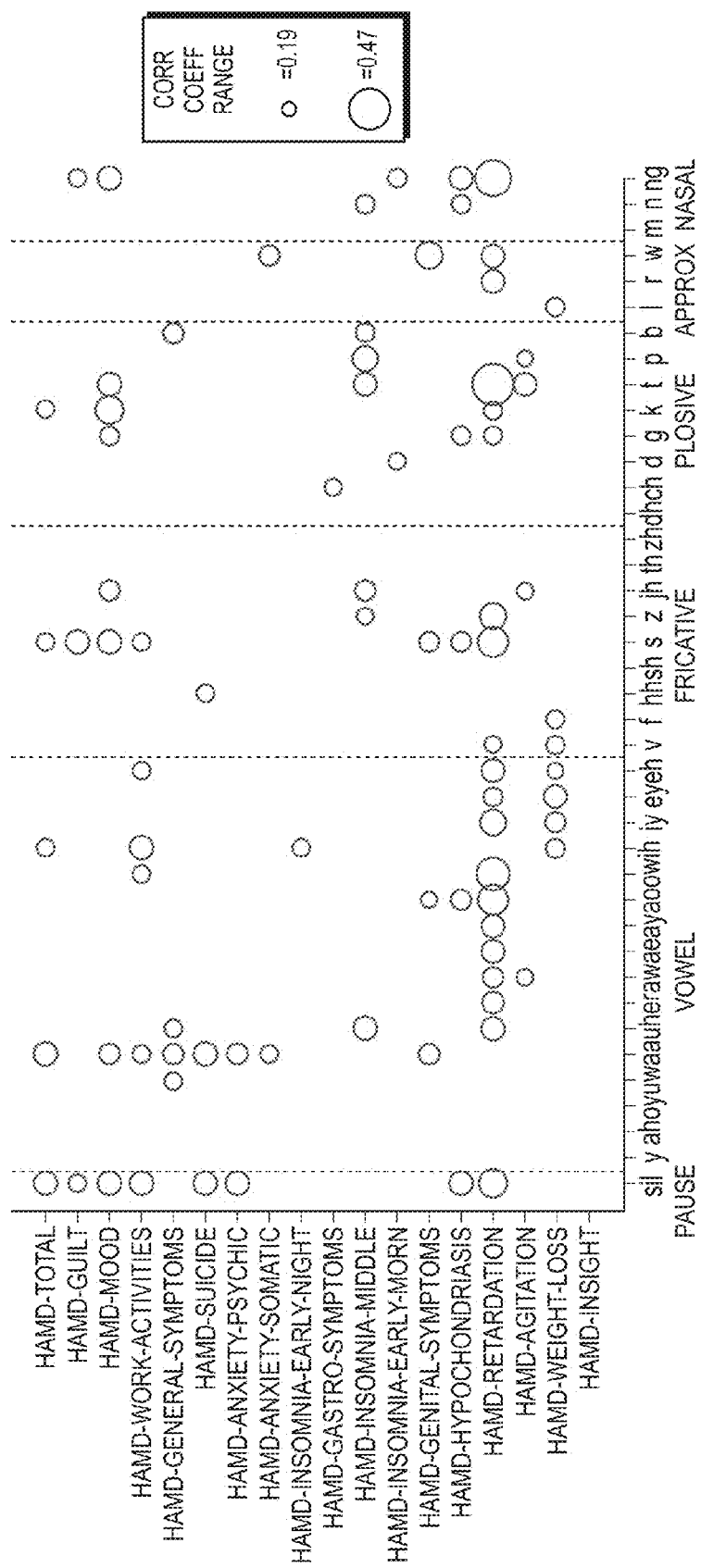
FIG. 5 is a plot of the correlation between individual phone length and HAMD score. Both positive and negative correlations are shown. The size of the circle marker is scaled by the magnitude of the correlation. Only significant correlations (p-value<0.05) are shown. Correlation coefficient range: max marker=0.47; min marker=0.19.

In order to test the correlation between specific phone characteristics and the sub-topic ratings of MDD, average length measures for each unique phone were extracted for each subject and session day. Significant correlations (i.e., correlations with p-value<0.05) across phones are illustrated in FIG. 5 for HAMD total and sub-topic ratings. It can be seen that the sign and magnitude of correlation varies for each symptom sub-topic, along with which of the specific phones show significance in their correlation value. A clear picture of the manner of speech (in terms of the phone duration) while certain symptoms are present can be inferred from FIG. 5.

The HAMD Psychomotor Retardation correlations stand out across a large set of phones, with positive individual correlations indicating a significant lengthening of these phones with higher Psychomotor Retardation rating. This is again consistent with the slowing of speech being an indicator of psychomotor retardation, but narrows down the phones which are affected to a small group, and reaches the high individual correlation of 0.47 with the average phone length of /t/. In contrast, there are also sub-topics that show groupings of phones that are significantly shortened with worsening of condition; for example, HAMD Insomnia Middle of the Night. Though there is some overlap in the unique phones that show significant correlations with ratings of condition, none of the total or sub-topic correlation patterns contain the exact same set of phones. Nonetheless, strong intercorrelations between the HAMD symptom sub-topics may be seen in the phone correlation patterns; for example, Psychomotor Retardation is most strongly correlated (negatively) with the Agitation subtopic; as a possible reflection of this, two phones that show a positive correlation with the Psychomotor Retardation sub-topic are negatively correlated with Agitation. The total HAMD score shows relatively low or no significant correlation values with the individual phone length measures, and the few that do show some significance create a mixed pattern of shortening and lengthening of those phones. Since the total assessment score is composed by taking the sum over all sub-topics, and each sub-topic seems to have a distinct lengthening or shortening speech rate pattern related to it, the total score should only show correlations with phone lengths that have consistent positive or negative correlations across a number of sub-topics; we see that this is the case, especially with pause length (/sil/) and the phones /aa/ and /s/.

An important consideration is the correlation patterns of phones that are produced in a similar way, i.e., have the same manner of articulation. FIG. 5 displays the phones in their corresponding groups; dashed vertical lines separate categories (vowel, fricative, plosive, approximant, nasal). Each category is described below.

Pauses are included in FIG. 5 for comparison. As noted, longer average pause lengths are measured with worsening of condition for a number of sub-topics.

Vowels—/aa/ and /uh/ are the two vowels that show more than one significantly negative correlation with a sub-topic, indicating shortening of duration with worsening of condition. There are two groups of vowels that show a positive correlation with HAMD Psychomotor Retardation score 1) the /aw/, /ae/, /ay/, /ao/, and /ow/ group, all which also fall into the phonetic category of open or open-mid vowels, and 2) the /iy/, /ey/, /eh/ group, which also has correlations with the Weight loss sub-topic (in addition to the Psychomotor Retardation sub-topic), this group falls into the phonetic category of close or close-mid vowels.

Fricatives—The fricative which has the most similar correlation pattern to any vowels is /v/, which is a voiced fricative. Consonants /s/ and /z/ both show lengthening (positive correlation) with worsening of Psychomotor Retardation; they are also both high-frequency fricatives. /s/ shows a consistent positive correlation pattern across a range of sub-topics, the correlation pattern for this fricative is most similar to the ones seen for pause length.

Plosives—With regard to Psychomotor Retardation, the three plosives which show significant positive correlations are /g/, /k/, and /t/, which are also all mid to high-frequency plosives; this group also shares similar correlations for the Mood sub-topic. A smaller effect, /t/ /p/ and /b/, all of which are diffuse (created at the front of the mouth, i.e., labial and front lingual) consonants, all show negative correlations with Middle of the Night Insomnia.

Approximants—Both /r/ and /w/ show a positive correlation with Psychomotor Retardation. The single significant correlation found for /l/ is with the Weight Loss sub-topic, which has no other correlation within the approximant group, but does show consistent correlations with a subset of the vowel (/ih/, /iy/, /ey/, /eh/) and fricative (/v/, /f/) groups.

Nasals—The nasal /m/ had no significant correlations with HAMD rating. The nasal /n/ has two significant correlations, but does not have similar correlation patterns to any other phone. The phone /ng/ has a correlation pattern most similar to /s/ and pauses.

The operation of example embodiments of the methods and systems of the present invention will now be explained with references to FIG. 6A through FIG. 6B.

Figure 6A:
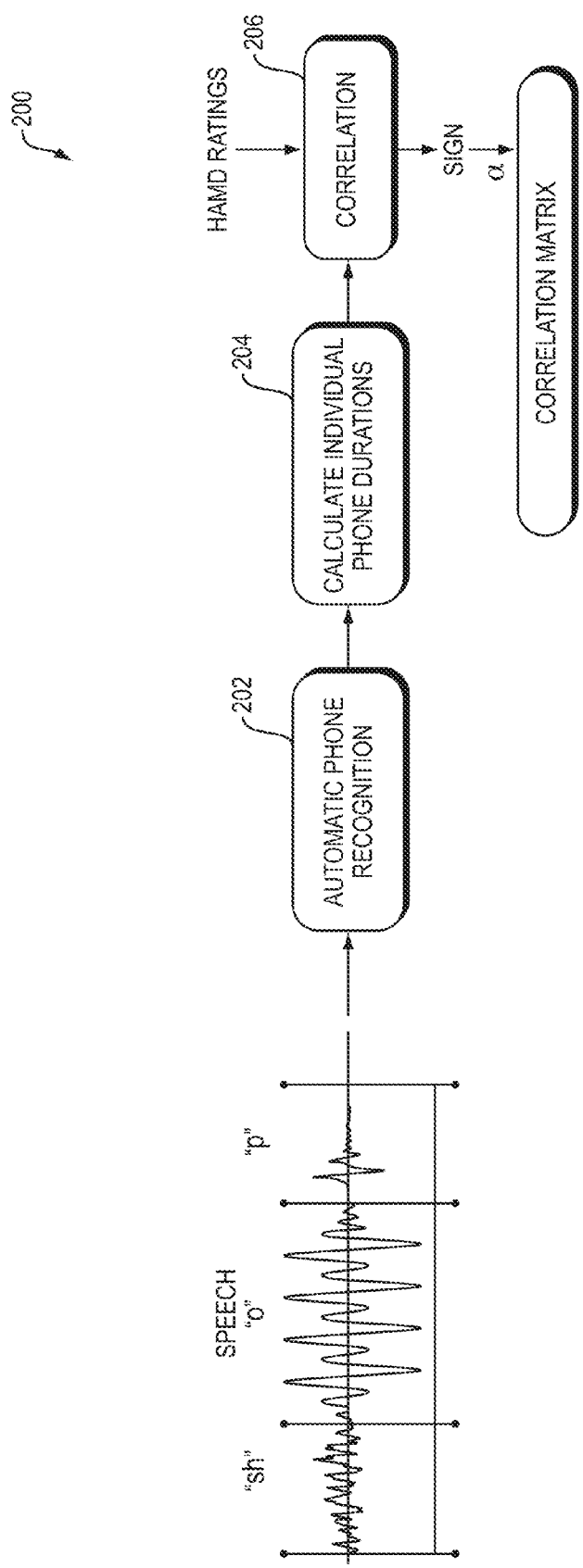
FIG. 6A is a schematic diagram of an example embodiment of a system of the present invention.

FIG. 6A shows a schematic diagram of an example system 200. System 200 operated to generate a correlation matrix, which included correlation coefficients between the features of the phones and a condition of interest. In the example shown in FIG. 6A, the correlation matrix was generated from speech. A series of speech recordings was used during training, each consisting of a speech waveform and an associated HAMD score. System 200 included an automatic phone recognizer 202, an individual phone duration calculation unit 204, and a correlator 206. Automatic phone recognizer 202 took each input speech waveform and outputted a stream of symbols representing phones, as well as their start and end times. Individual phone duration calculation unit 204 took an input stream of phone symbols, phone start times, and phone end times. It outputted a stream of durations. Duration was calculated for each phone as the phone end time minus the phone start time. For each different phone symbol, a mean duration was calculated by averaging all of the durations for that phone type. Correlator 206 takes as input a series of mean phone durations for each waveform as well as the HAMD score for each waveform. Correlation coefficients were calculated, relating HAMD score to each of the phone durations, for example. The output was a matrix of correlation coefficients, or a matrix of weighting coefficients that described values, derived from the correlation coefficients, by which to combine mean phone durations.

Figure 6B:
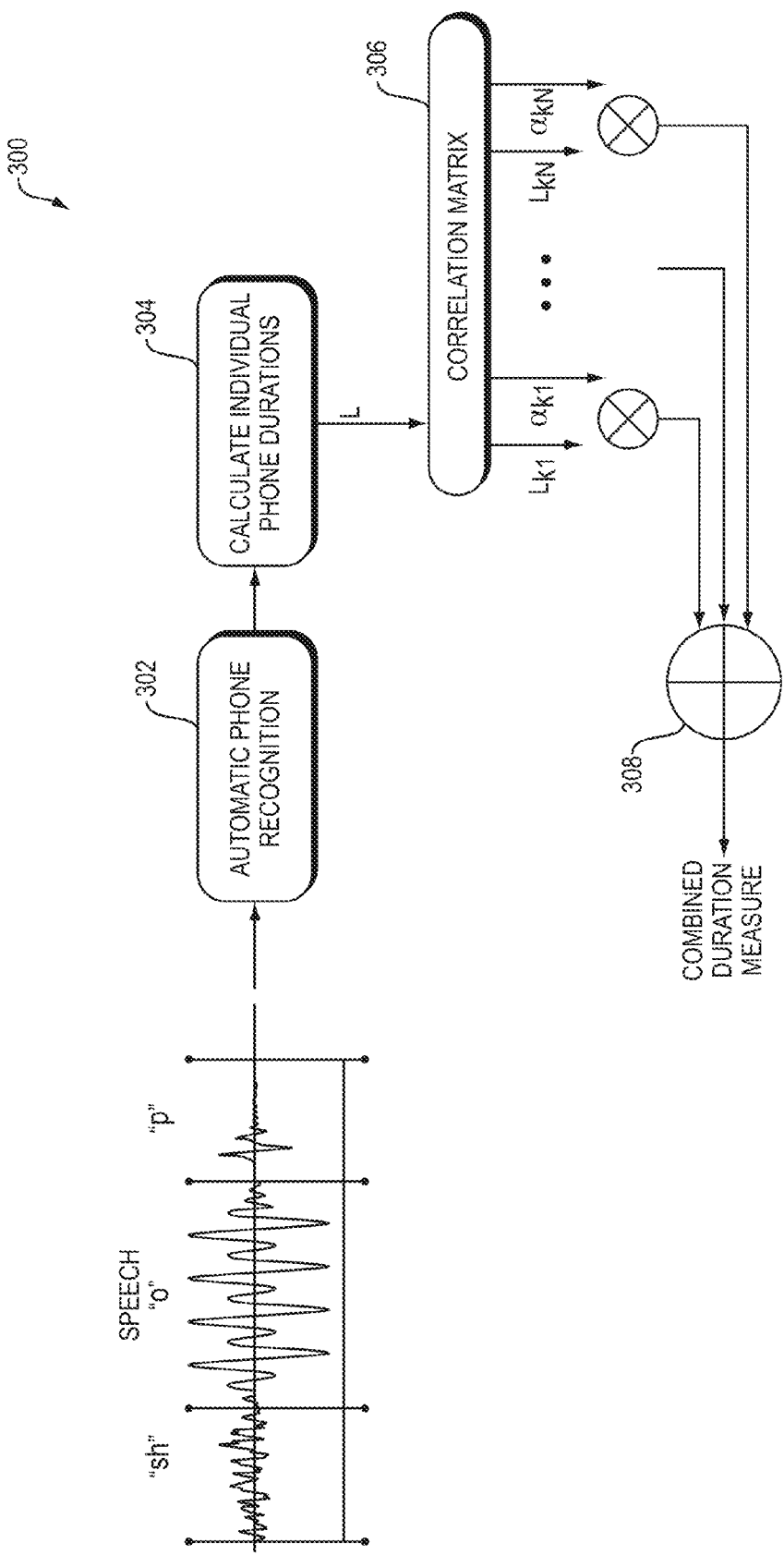
FIG. 6B is a schematic diagram of an example embodiment of a system of the present invention.

FIG. 6B shows a schematic diagram of an example system 300. System 300 operated to generate an assessment of a condition of interest in a subject. System 300 included an automatic phone recognizer 302, an individual phone duration calculation unit 304, a correlation matrix logic unit 306 and a combination logic unit 308. In the example shown in FIG. 6B, a speech recording was used to estimate a HAMD score of a subject using a correlation matrix generated by the system 200 illustrated in FIG. 6A. Combination logic unit 308 took each input speech waveform and outputted a stream of symbols representing phones, as well as their start and end times. Individual phone duration calculation unit 304 took an input stream of phone symbols, phone start times, and phone end times. It outputted a stream of durations. Duration was calculated for each phone as the phone end time minus the phone start time. For each different phone symbol, a mean duration was calculated by averaging all of the durations for that phone type. Correlation matrix logic unit 306 applied the correlation matrix to obtain a combined duration measure of the condition of interest. Combination logic unit 308 weighed each phone-dependent mean "duration" by the associated value in the correlation matrix and combined the outputs to form a combined duration measure used to estimate the HAMD score of the subject.

Figure 6C:
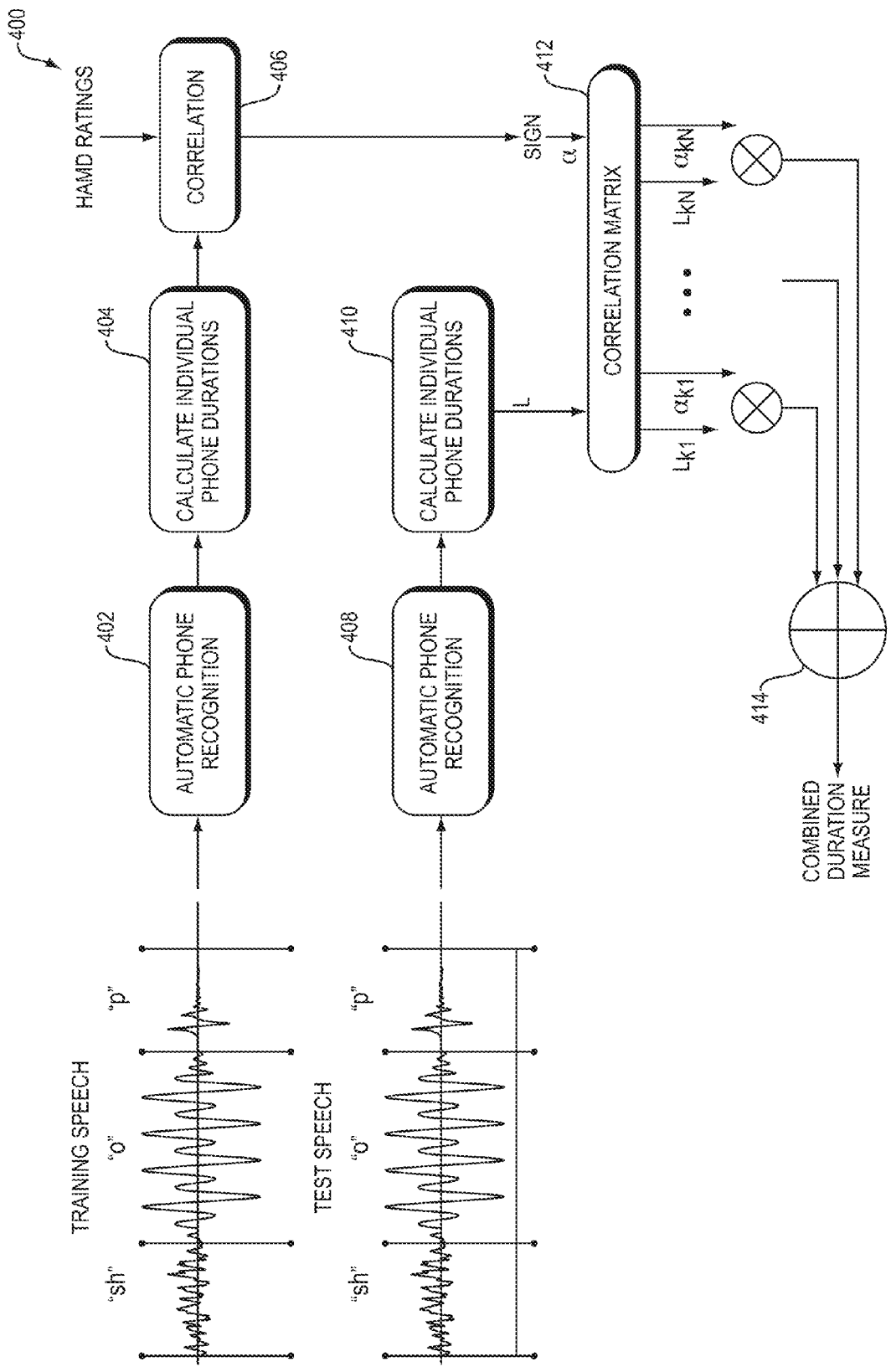
FIG. 6C is a schematic diagram of an example embodiment of a system of the present invention.

FIG. 6C shows a schematic diagram of an example system 400. System 400 operated to generate a correlation matrix, which included correlation coefficients between the features of the phones and a condition of interest, and to generate an assessment of a condition of interest in a subject. System 400 included an automatic phone recognizer 402, an individual phone duration calculation unit 404, and a correlator 406. The system can also optionally include a second automatic phone recognizer 408, and a second individual phone duration calculation unit 410. Alternatively, the function of units 408 and 410 can be performed by units 402 and 404, respectively. System 400 further includes a correlation matrix logic unit 412 and a combination logic unit 414.

The example embodiment illustrated in FIG. 6C was operated in both training (correlation matrix-generating) phase (mode) and assessment-generating phase (mode). The system was first be trained using speech and associated HAMD scores of one or more control subjects. Then, in the assessment mode, speech was used to estimate a HAMD score of a test subject. In the training mode, automatic phone recognizer 402 took each input speech waveform and outputted a stream of symbols representing phones, as well as their start and end times; individual phone duration calculation unit 404 took an input stream of phone symbols, phone start times, and phone end times. It outputted a stream of durations. Duration was calculated for each phone as the phone end time minus the phone start time. For each different phone symbol, a mean duration was calculated by averaging all of the durations for that phone type. Correlator 406 took as input a series of mean phone durations for each waveform as well as the HAMD score for each waveform. Correlation was calculated, relating HAMD to each of the phone durations. The output was a matrix of weighting coefficients that describes values, derived from the correlations, by which to combine mean phone durations.

In the assessment mode, automatic phone recognizer 402 or second automatic phone recognizer 408 took each input speech waveform and outputs a stream of symbols representing phones, as well as their start and end times; individual phone duration calculation unit 404 or second individual phone duration calculation unit 410 took an input stream of phone symbols, phone start times, and phone end times. It outputted a stream of durations. Duration was calculated for each phone as the phone end time minus the phone start time. For each different phone symbol, a mean duration was calculated by averaging all of the durations for that phone type. Correlation matrix logic unit 412 applied the data structure of weights that describe how to combine mean durations in order to obtain a combined duration measure. Combination logic unit 414 weighed each phone-dependent mean "duration" by the associated value in the correlation matrix and combined the output to form a combined duration measure used to estimate the HAMD score.

In a further illustration of the example embodiments of the methods and systems of the present invention, sub-topics with at least four significant individual phone correlations were identified and linearly combined into a measure (a combined weighted duration). Positive or negative unit weights were chosen based on the sign of their individual phone correlation values. The average length of k-th phone, denoted by $L_k$ was computed, and a subset $P_i$ of significantly correlated average phone lengths for the i-th HAMD subtopic was selected. The sign-weighted "duration measure" of the i-th HAMD sub-topic was then computed as the sum $$L^i = \sum_k \alpha_k L_k \;\; k \ni P_i$$

where the weighting coefficients $\alpha_k$ were ±1, defined by the sign of the relevant phone correlation.

Through this simple linear combination of a few phone-specific length features we are able to achieve much higher correlations than when examining average measures of the speech (i.e., globally), and, as before, the highest correlation is reached by the HAMD Psychomotor Retardation sub-topic.

Applying the systems illustrated in FIGS. 6A-6C, the correlation between the weighted sum of the individual phone lengths and the relevant score was obtained and is shown in FIG. 7, which presents Table III. The left-most column gives the set of phones used for each sub-topic (selected based on correlation significance). The largest correlations are achieved by the "optimally" selected composite phone lengths with each sub-topic. The largest correlation of the composite phone lengths is again reached by the HAMD Psychomotor Retardation measure with a value of 0.58, although the gain in correlation value from 0.47 (achieved with /t/) to 0.58 is small considering the large number of phones that contribute to the composite feature (19 phone durations and pause/silence duration). In contrast, for the HAMD Work and Activities sub-topic, a correlation gain from 0.28 (/ih/) to 0.39 (/sil/ /aa/ /ih/ /ow/ /eh/ /s/) is achieved using only 6 phone lengths in the composite feature.

Figure 8:
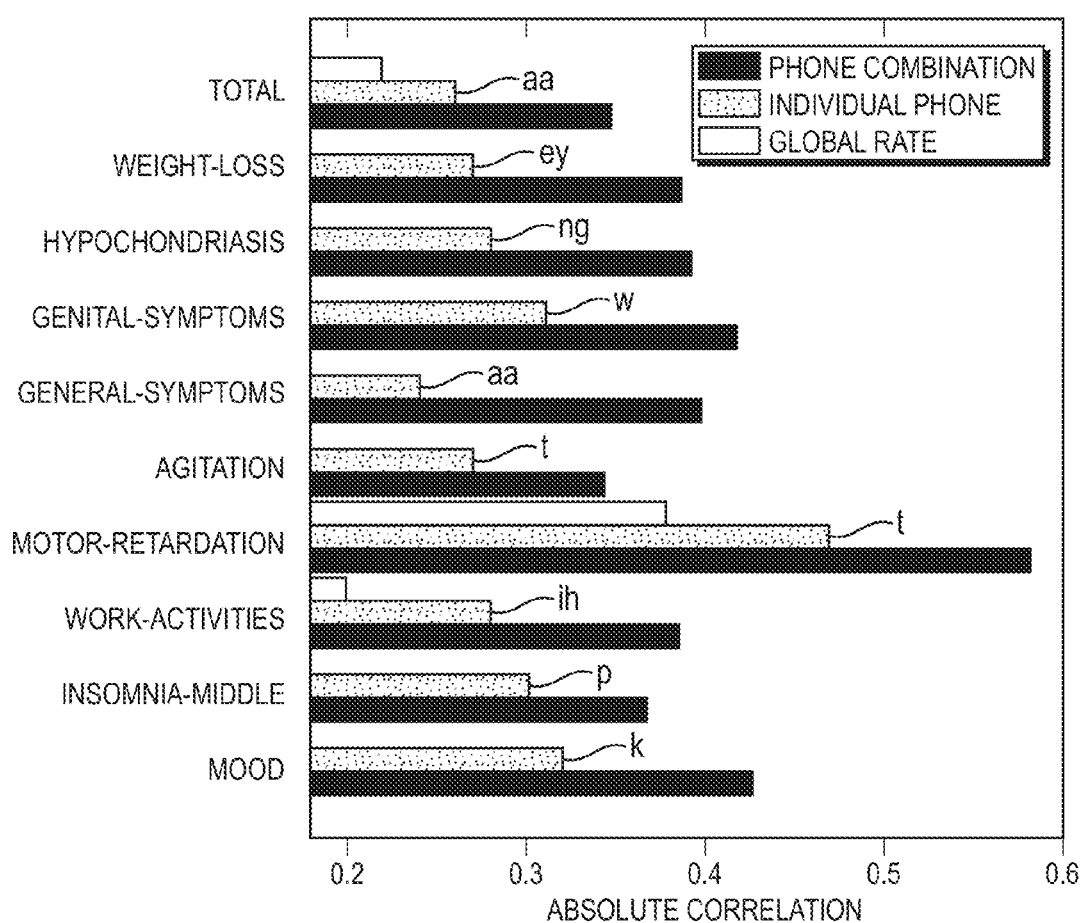
FIG. 8 is a bar plot showing a comparison between the highest individual phone correlation and the composite length feature correlation values from FIG. 7 (Table III).

An alternative view of the correlation results of FIG. 7 (Table III) is shown in FIG. 8. FIG. 8 is a bar plot showing a comparison between the highest individual phone correlation and the composite length feature correlation values from FIG. 7 (Table III). Significant correlations with global speaking rate (from FIG. 3, Table I) are included for comparison. FIG. 8 shows absolute Spearman correlation value between the measure of the phone length and HAMD score. The individual phone correlation bars correspond to the maximum absolute correlation between depression assessment score and a single phone-specific average length; the specific phone used is shown at each bar. The phone combination correlation bars show the absolute correlation value between assessment score and the signed aggregate phone length; the phones used for this aggregate length are listed in the first column of Table III in FIG. 7. Global speaking rate correlation values from FIG. 3 (Table I) are included for comparison.

Figure 9:
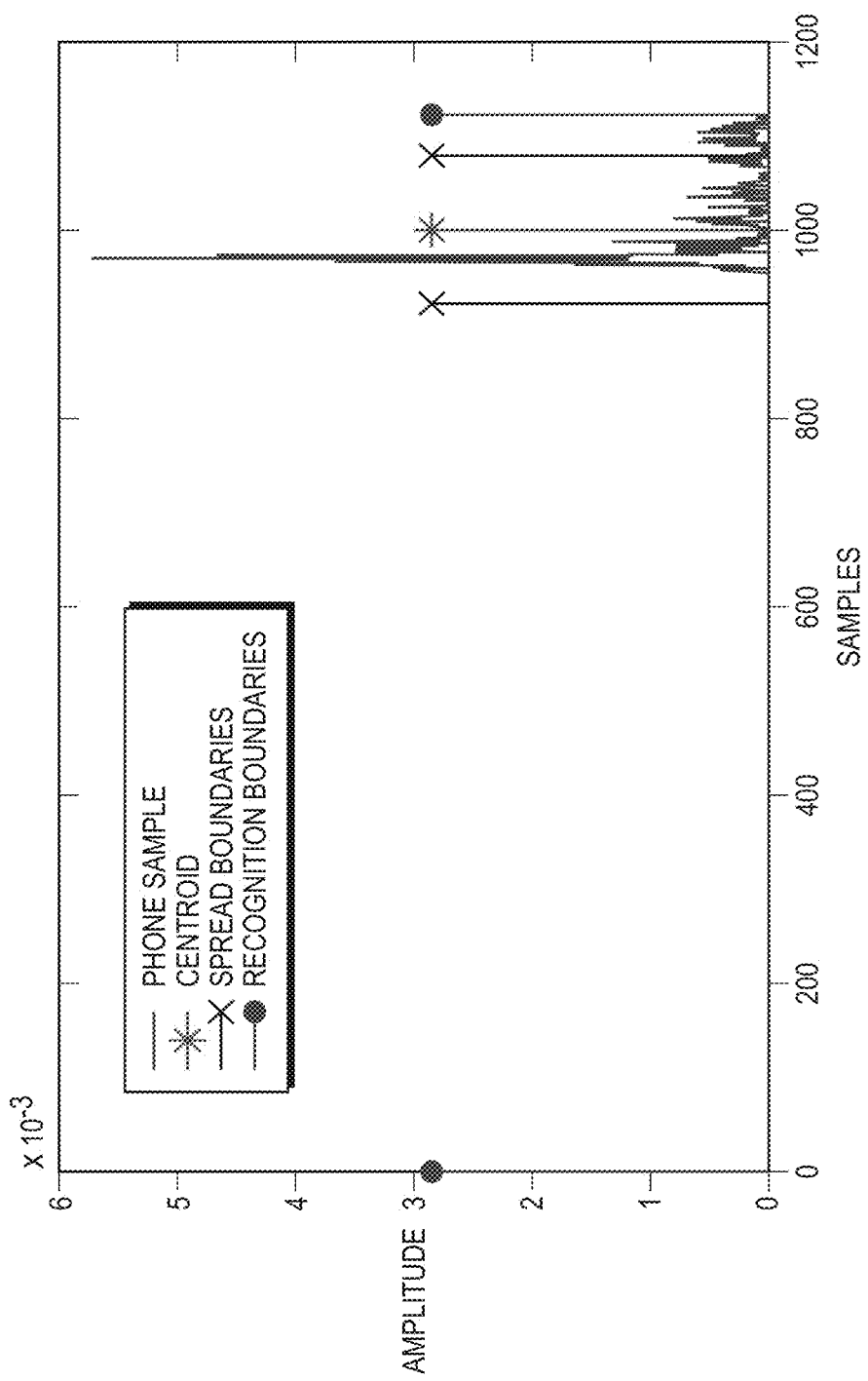
FIG. 9 is a plot showing amplitude of a burst consonant /t/ as a function of time (i.e. samples taken at the rate of 8 kHz).

An alternative definition of phone duration was constructed using the concept of the spread of a signal's energy. A large subset of the phones consists of a single, continuous release of energy with tapered onset and offsets, particularly the case with burst consonants (e.g., /p/, /b/, etc.) and vowel onsets and offsets. FIG. 9 presents an example: the amplitude of a consonant /t/ as a function of time. This is an example of a single utterance of the burst consonant /t/ where the boundaries detected by the automatic phone recognizer are greater than the phone duration corresponding to energy spread. Asterisk and cross markers show our estimated centroid and spread boundaries for this phone.

In these cases, phone boundaries, as deduced from an automatic phone recognizer, may not provide an appropriate measure of phone duration. One measure of phone length or duration is given by the signal spread about the centroid of the envelope of a signal, described, e.g., in Quatieri, T. F., *Discrete-Time Speech Signal Processing: Principles and Practice*, Prentice Hall, 2001, the relevant teachings of which are incorporated herein by reference.

The centroid of the phone utterance, denoted e[n], is computed via a weighted sum of the signal. Specifically, the centroid for each phone utterance, $n_{centroid}$, is given by $$n_{centroid} = \sum_{n=1}^{N} n \frac{e[n]^2}{\sum_{m=1}^{N} e[m]^2}$$

where the square of the signal is normalized to have unit energy and where N is the number of samples in each phone utterance. The standard deviation about $n_{centroid}$ is used as the 'spread' (i.e., alternate duration) feature. The spread of a single phone utterance is thus calculated as $$\text{spread} = \sqrt{\sum_{n=1}^{N} (n - n_{centroid})^2 \frac{e[n]^2}{\sum_{m=1}^{N} e[m]^2}}$$

Figure 10:
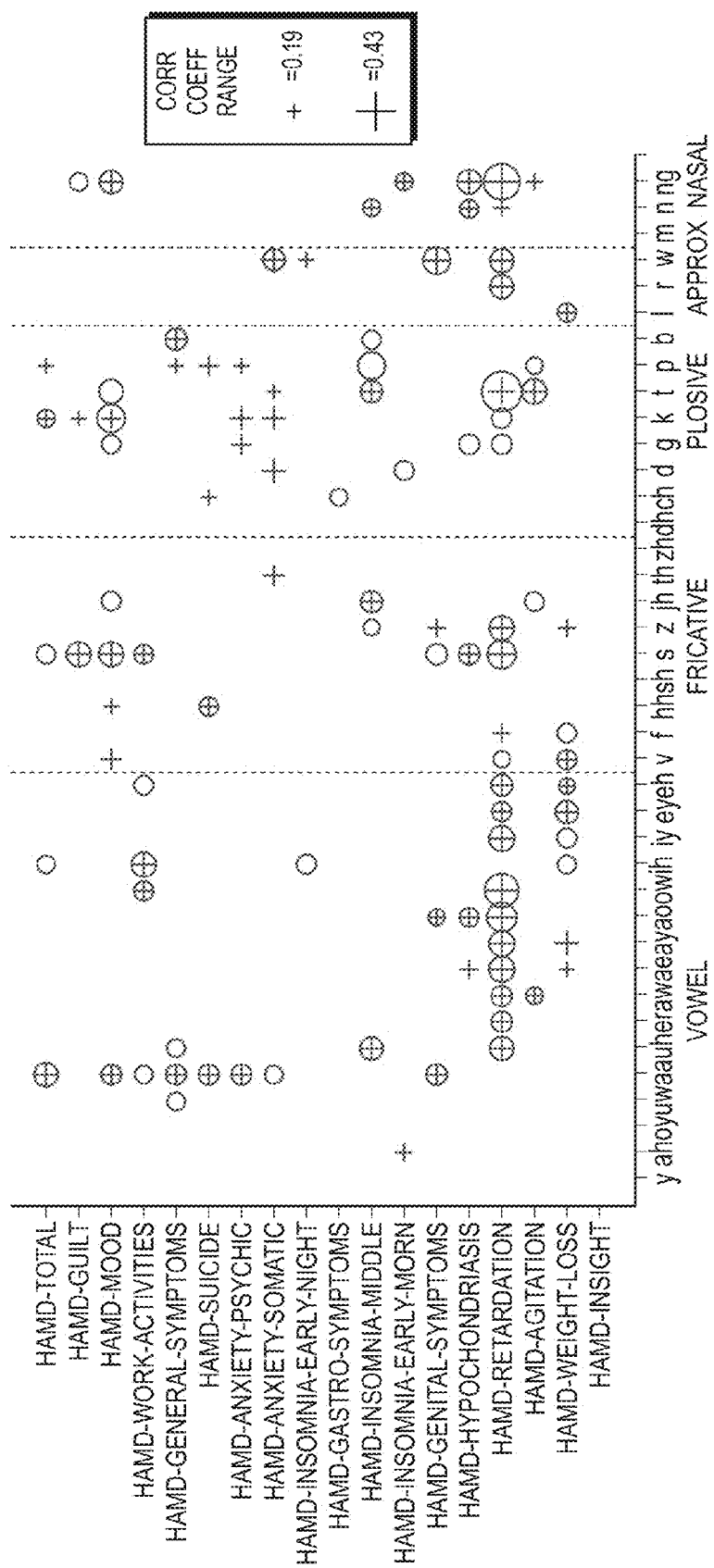
FIG. 10 is a scatter plot showing a comparison between the spread and recognition-derived length correlations with depression rating.

Significant spread-based phone length correlations are illustrated in FIG. 10 for both HAMD total and sub-topic ratings. FIG. 10 is a scatter plot showing a comparison between the spread and recognition-derived length correlations with depression rating. Spread correlations are marked with a cross, recognition-based length correlations are marked with a circle. Both positive and negative correlations are shown. The size of the marker is scaled by the magnitude of the correlation. Only significant correlations (p-value<0.05) are shown. Correlation coefficient range: max cross marker=0.43; min cross marker=0.19. Range of circles is the same as in FIG. 5.

It can be seen that HAMD Psychomotor Retardation stands out with a large set of significant positive correlations with phone duration, indicating longer durations with worsening of condition. HAMD Insomnia Middle of the Night shows consistent shortening of phone duration with increasing severity ratings. This consistency with the recognition-based length results is a product of the strong correlation between our recognition and spread-based measures. It can be seen that overall there are more changes in the correlation results with burst consonants, such as /k/, /g/, and /p/, than with any other phones due to their burst-like, shorter nature in time. As seen in FIG. 9, the phone recognition algorithm showed a tendency to overestimate (set too early) the onset phone boundary for these burst consonants; on the other hand, the duration of the silence gap prior to or after the burst may also be condition-dependent.

One of the more general relationships that can be drawn from the data presented above is that worsening of psychomotor retardation condition can be observed in a subject's speech rate. A question can be asked whether the correlations between the speech measures and the other sub-topics result from noise and/or sub-topic intercorrelation with the Psychomotor Retardation sub-topic. In order to reduce the effects of spurious correlations on the interpretation of results, in addition to only showing significant results, the phones are grouped according to manner of articulation and the sub-topics are grouped by significant absolute intercorrelation values. Clustering of significant correlations within a phonetic or intercorrelation sub-group suggests that these consistent correlations are indeed meaningful.

For further applications, one needs to know which correlation results are the product of strong intercorrelation between each sub-topic and Psychomotor Retardation and which are not. To help address this, an additional experiment was run where the correlations between sub-topics and phone length were re-computed using only the speaker-session samples that had a Psychomotor Retardation score of 0 (i.e., no recorded psychomotor retardation). The results are shown in FIG. 11.

Figure 11:
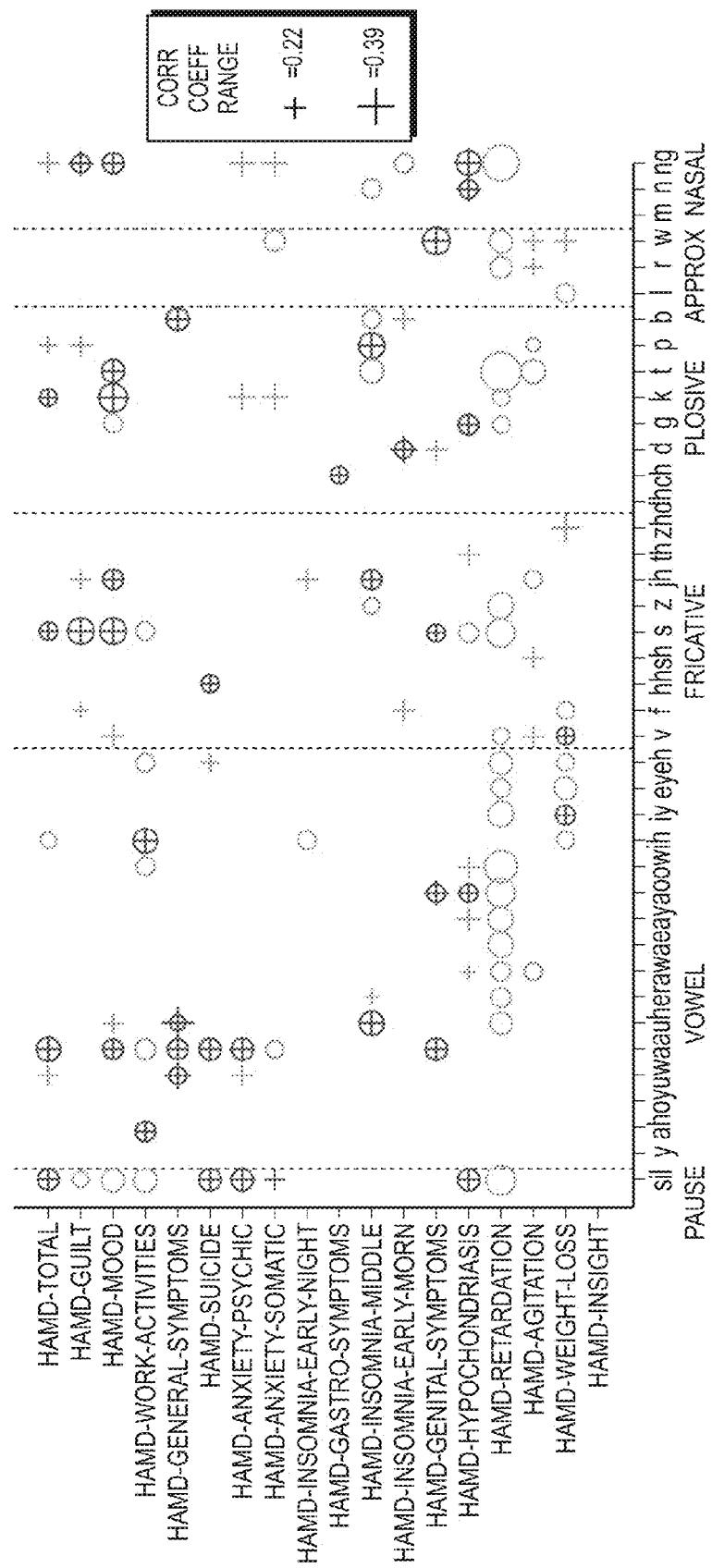
FIG. 11 is a scatter plot showing a comparison between the individual phone length correlations of FIG. 5 (circle marker) and the individual phone length correlations when all samples showing a nonzero Psychomotor Retardation rating are removed from the calculation (cross marker).

FIG. 11 is a scatter plot showing a comparison between the individual phone length correlations of FIG. 5 (circle marker) and the individual phone length correlations when all samples showing a nonzero Psychomotor Retardation rating are removed from the calculation (cross marker). Correlations which are not significant in both cases are faded for visualization. Both positive and negative correlations are shown. The size of the marker is scaled by the magnitude of the correlation. Only significant correlations (p-value<0.05) are shown. Correlation coefficient range: max cross marker=0.39; min cross marker=0.22.

It can be seen from FIG. 11 that for sub-topics that are strongly correlated with Psychomotor Retardation, such as Agitation and Work-Activities (see FIG. 2), the correlation patterns do change and most of the significant correlations found earlier are no longer present. For sub-topics that have a weak correlation to Psychomotor Retardation, such as Suicide or General Symptoms, many of the previous significant correlations found with phone length remain the same. In addition, for all correlations that are retained with this second analysis there is no change in sign, further supporting the hypothesis that these correlations are not spurious or completely due to intercorrelations with Psychomotor Retardation.

As mentioned earlier, the phone recognition algorithm is based on a Hidden Markov Model approach, which for English was reported as having about an 80% overall accuracy. Although this implies some mislabeling of phones, the mislabeling is often between similarly structured (i.e. similar in time and frequency) phones. The primary effect of labeling errors is a form of added 'noise' to this correlation study and the feature vectors that will be discussed below. In spite of this noise inclusion, strong correlations with phone-specific length features were found. This discovery is the basis for preliminary classification work described below.

The results presented herein could be used to develop an automatic classifier of depression severity based on phone-specific measures of speech rate. As an initial step toward this goal, a proof-of-concept use of speech rate features was demonstrated. Specifically, the set of recognition-derived, phone-specific lengths, was used for classification.

In forming depression classifiers, a 5-class problem for the HAMD total score was considered. The 5-class case was divided into the ranges 0-5, 6-10, 11-15, 16-20, and 21-27. A 5-class experiment demonstrated a test of classification accuracy. For the symptom sub-topics, the 3, 4, or 5-class problem were implemented for each sub-topic based on the maximum possible range for each. For example, the HAMD Mood sub-topic has the possible scores of 0, 1, 2, 3 or 4, thus a 5-class problem was implemented for this sub-topic. For all classifiers considered, the tests employed a leave-one-out cross validation scheme, as illustrated schematically for a 2-class case in FIG. 12.

Figure 12:
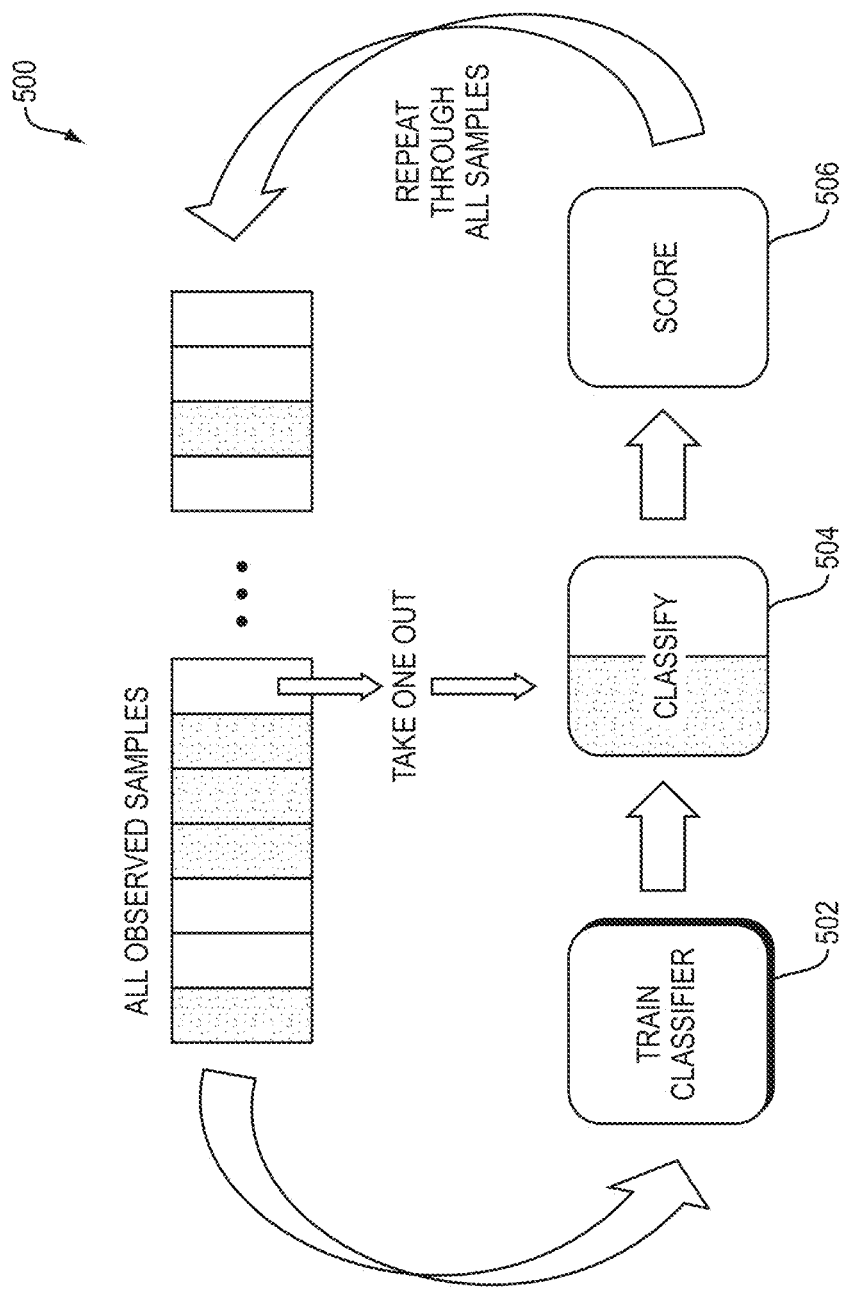
FIG. 12 shows an example classification method of the present invention.

FIG. 12 shows an example classification method of the present invention. Method 300 includes step 302 of training the classifier, step 304 of classifying and step 306 of generating a score (e.g. a measure of a condition). Specifically, FIG. 12 illustrates the leave-one-out cross-validation approach for the 2-class problem, depicted as light shading vs. dark shading. Each unique subject-session pair in the dataset is an "observed sample" that is described by its feature vector. For cross validation, one sample was taken out, the classifier was trained on the remaining samples, the excluded sample was classified, and the performance was recorded. The process was repeated until all of the observed samples have been tested.

A simple Gaussian maximum-likelihood algorithm was used in all experiments, i.e., each class was modeled as a multi-dimensional Gaussian, with the number of dimensions matching the feature vector dimension. Classification was then performed by finding the class of maximum likelihood for the test sample. The phonological feature vector is composed of the recognition-derived average phone (vowels and consonants) lengths and the average pause (silence) length values. Four different feature selection methods were considered: 1) A single feature, the signed aggregate of individual phone lengths and pause length; 2) No feature selection, i.e., all individual average phone lengths and/or the pause length as a vector of features; 3) Hand-selection of the subset of individual phone lengths and/or pause length that showed significant correlation statistics to form a feature vector; and 4) A subset of individual phone lengths and/or the pause length automatically selected to minimize error, though an optimal solution was not guaranteed.

Providing classification results on the symptom sub-topics would add an additional level of feedback to a clinician. In addition, considering each rating level as a class takes into account the fact that variations on a single-point scale could indicate large changes in an individual's condition. Therefore, each sub-topic as a 3, 4, or 5-class problem was examined, with the number of classes matching the range of possible scores for each particular sub-topic. The total scores were divided into a 5-class problem in order to test the classifier's ability to differentiate between in remission, mild, moderate, severe, or very severe depression.

Figure 13:
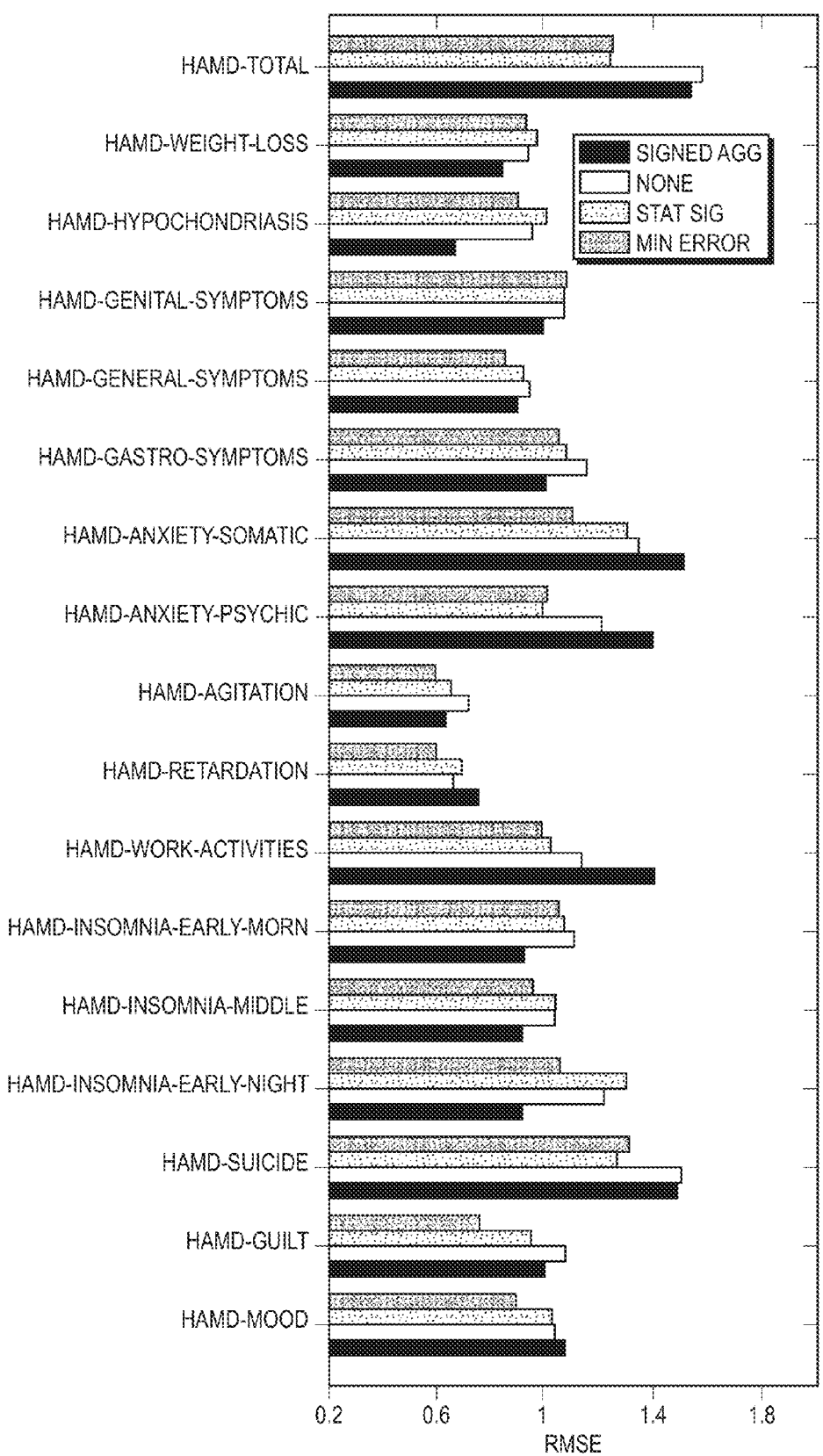
FIG. 13 is a bar plot which shows the Adjusted Root Mean Squared Error (RMSE) for each individual HAMD sub-score.

It was found that most of the classification errors come from misclassification into an adjacent severity level, for example a severity rating of 1 for a given sub-topic might be misclassified as a 0 or a 2. These results are summarized in FIG. 13, which shows the Adjusted Root Mean Squared Error (RMSE) for each individual HAMD sub-score. RMSE is defined as the average over the RMSE for each rating value, giving each an equal weight, to account for some highly skewed distributions of observed data. In FIG. 13, different shading of the bars indicate the method of feature selection, 'none' being no feature selection (i.e. all phone length features used).

The RMSE gives a sense of how far the classifier diverges from the clinician or self-reported rating; all of the RMSEs fell below 2, quantifying the observation that most misclassifications fall into an adjacent severity level. In almost all cases, some form of feature reduction is beneficial; features that were hand-selected from the correlation resulted in overlap but did not exactly match the features that were chosen by the algorithm to minimize error. Finally, the RMSEs indicated the predictive potential of the phonologically-based feature sets including the single feature of linearly combined duration.

The studies presented herein give direction in determining which speech-rate-based vocal features may be useful for detecting depression symptoms. For all of the cases under investigation, a phone-specific approach showed higher correlations than the global rate measurements. Pause length was considered separately from vowel/consonant length due to the different factors that can affect the two types of features; it was assume that pause length incorporates both psychomotor issues along with possible hesitancy due to other depression symptoms. The usage of energy spread to define phone duration provides an alternate scheme for computing phone duration, not tied strictly to automatic recognition-based phone boundary definitions. The phone and symptom-specific correlation patterns present a visual interpretation of how speech can change with different symptom severities. Possibly, speech sounds with either similar production categories or similar usages in speech (e.g., at the onset or at the ending of a word) would show correspondingly similar changes with MDD condition severity; we explored the former by grouping the phones by manner of articulation and finding consistencies in the correlations within the groups. Other experiments that indicated that not all meaningful sub-topic correlations are tied to Psychomotor Retardation involved correlations between sub-topics and phone length re-computed using only the speaker-session samples that had a Psychomotor Retardation score of 0. The additional correlation study with the linearly combined phone duration measure shows how using only a subset of phones can reveal a stronger underlying relationship.

It is also possible that HAMD sub-topics with similar or correlated symptoms would show similarities in the shift in speech rate and phone-specific duration measures. The similarities between symptom sub-topics were quantified by the intercorrelations shown in FIG. 2. As an example analysis, the Psychomotor Retardation sub-topic was examined. This sub-topic is most strongly correlated with Agitation (negatively, −0.40) and Mood (positively, 0.36). FIG. 5 shows oppositely-signed significant correlations for both Psychomotor Retardation and Agitation for 2 phones (/aw/, /t/); FIG. 5 also shows positive significant correlations for both Psychomotor Retardation and Mood for the same 5 phones and the pause measure (/sil/, /s/, /g/, /k/, /t/, /ng/). The strongest HAMD intercorrelation for the dataset used in this study fell at 0.64 and corresponded to the correlation between the Mood and Work-Activities sub-topics. Although the correlation patterns for these phonologically-based measures share some characteristics, they are not the same, indicating that the two sub-topics are somewhat distinct.

The classification results presented herein reveals changes that occur in speech rate with different symptom severities. Some symptoms, such as Psychomotor Retardation, had a consistent relationship with a change in speech pattern, while others, such as short-term changes in Weight, did not. Identifying reliable biomarkers for each symptom is useful, since each symptom category and progression to different severities is more homogeneous across patients than the overall depression rating, which can encompass completely different manifestations of the disorder.

Based on the success of phone-specific speech rate measures in correlating with certain MDD symptoms, the methods presented herein can be extended to examining other phone-specific speech measures. Examples include phone-specific energy measures, an examination of vowel usage in depression, and measures involving prosodic rhythm and modulation, and using the derivative of measures. The derivative of a vocal feature allows one to track how the changes in an individual's speech pattern may match similarly scaled changes in their condition. Use of derivatives also serves as a way to normalize out absolute levels in a subject's baseline speech.

For example, the speaking and articulation rate, as defined above, were calculated with respect to the "pseudo-syllable rate" and correlations with HAMD scores were computed. To compute the "pseudo-syllable rate," individual phones were combined such that each vowel forms the nucleus of its own segment, with all of the proceeding consonants grouped with it. The motivation for this unit is its relation to syllables and the difficulty in automatically extracting syllables. Similar to the phone rate results, the pseudo-syllable speaking rate showed significant correlation with the HAMD Psychomotor Retardation (−0.37) and total (−0.26), and the pseudo-syllable articulation rate showed highly significant correlation with the Psychomotor Retardation rating (−0.41).

Figure 14:
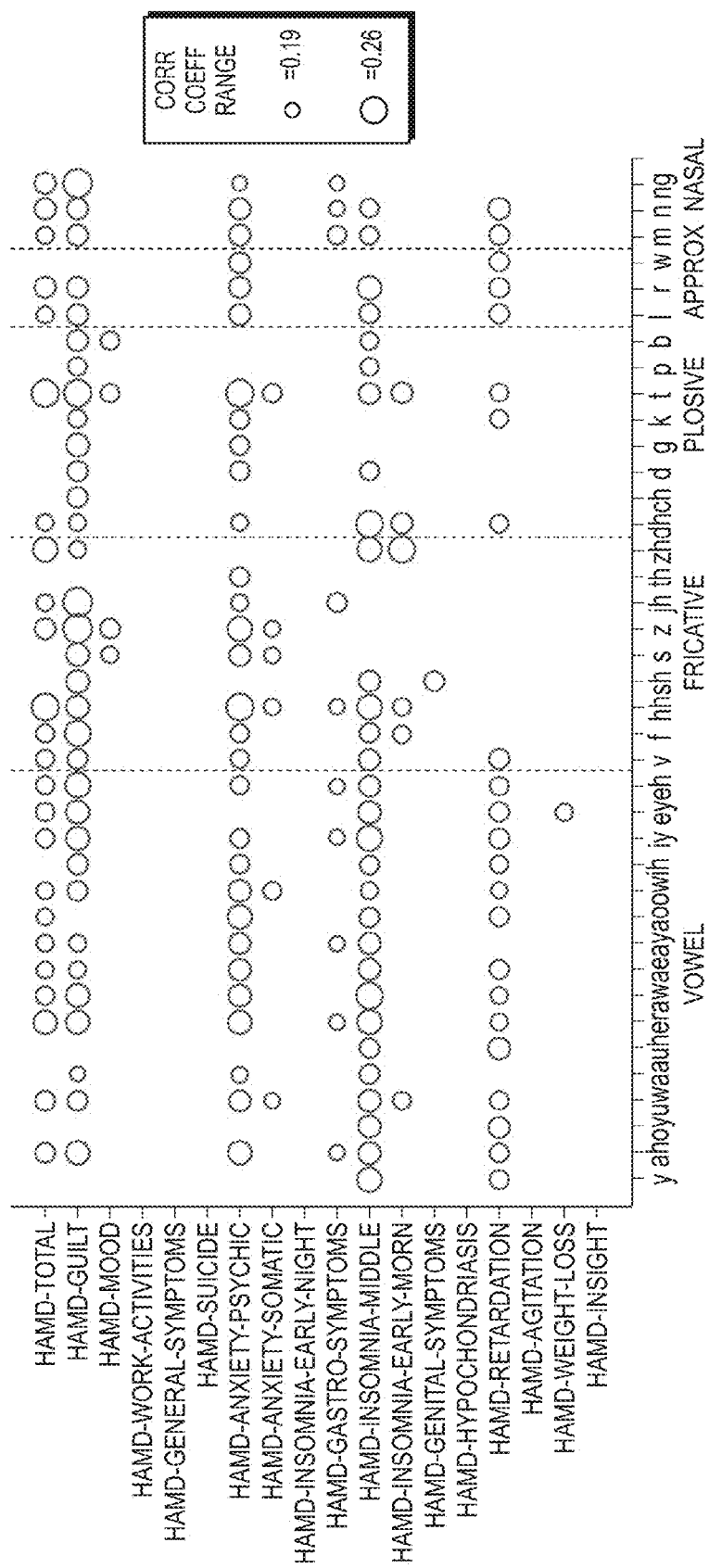
FIG. 14 a scatter plot showing correlation between individual phone average power and HAMD score.

FIG. 14 a scatter plot showing correlation between individual phone average power and HAMD score. Both positive and negative correlations are shown. The size of the circle is scaled by the magnitude of the correlation. Only significant correlations (p-value<0.05) are shown. Correlation coefficient range: max marker=0.26; min marker=0.19. In FIG. 14, Phone power is computed as the sum of the squared signal over time. We see that the significant correlations with phone power are more uniform across phones within a sub-topic. Correlations with Psychomotor Retardation are negative for all phones and limited to mostly the vowel, approximant and nasal phone categories.

Figure 15:
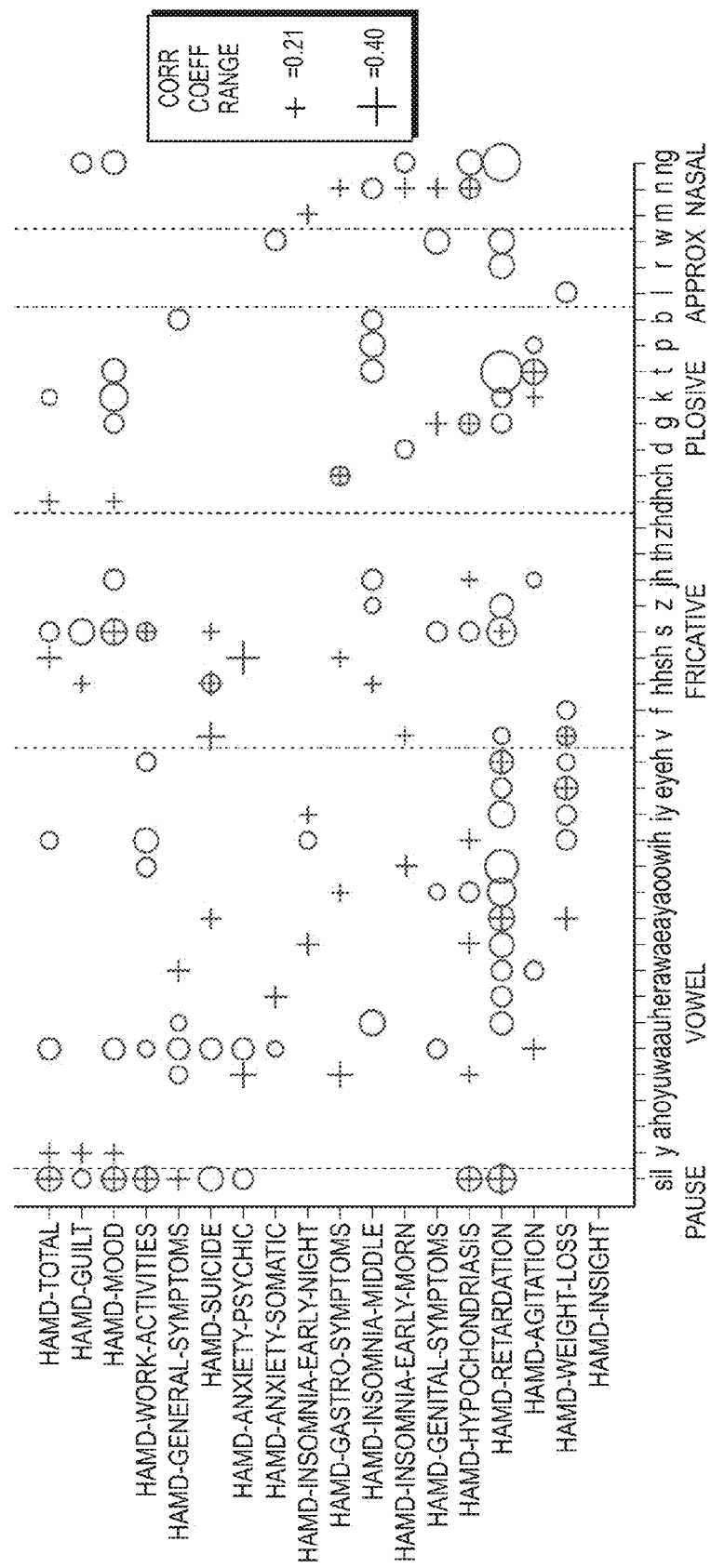
FIG. 15 show a plot comparing the correlations between the individual phone length (as in FIG. 5) and the HAMD scores and the corresponding derivatives of the phone lengths.

FIG. 15 show a plot comparing the correlations between the individual phone length (as in FIG. 5) and the HAMD scores and the corresponding derivatives of the phone lengths. Derivative correlations are marked with a cross, base value correlations are marked with a circle. Both positive and negative correlations are shown. The size of the marker is scaled by the magnitude of the correlation. Only significant correlations (p-value<0.05) are shown. Correlation coefficient range: max cross marker=0.40; min cross marker=0.21.

A derivative of the vocal features was computed by measuring the relative change between feature values on consecutive session days for each subject. The corresponding derivative of the depression ratings was computed in the same way. Comparing the derivatives results with the base value phone-specific correlations, there are no inconsistencies in the direction of length change with severity of condition; in other words, for all overlapping significant correlations, no positive correlation in one study is negative in the other.

HAMD sub-topics: The range of score for each is included in parenthesis; higher scores indicate a worsening of condition.

1) Depressed Mood (0-4)—Sadness, hopeless, helpless, worthless, along with the person's inability to hide these feelings
2) Feelings of Guilt (0-4)—Magnitude of guilt
3) Suicide (0-4)—Thoughts of suicide along with severity of attempts
4) Insomnia: Early in the Night (0-2)—Difficulty falling asleep
5) Insomnia: Middle of the Night (0-2)—Waking during the night
6) Insomnia: Early Hours of the Morning (0-2)—Early waking and inability to return to sleep
7) Work and Activities (0-4)—Thoughts or feelings of fatigue and level of interest in work or activities 8) Psychomotor Retardation (0-4)—Slowness of thought and speech, impaired ability to concentrate, decreased motor activity
9) Agitation (0-4)—Physical inability to sit still
10) Anxiety Psychic (0-4)—Level of expression of anxiety
11) Anxiety Somatic (0-4)—Physiological concomitants of anxiety
12) Somatic Symptoms Gastro-intestinal (0-2)—Loss of appetite, heavy feeling in abdomen
13) General Somatic Symptoms (0-2)—Heavy limbs, muscle aches, headache, fatigue
14) Genital Symptoms (0-2)—Loss of libido, menstrual disturbances (for women)
15) Hypochondriasis (0-4)—Magnitude of hypochondria
16) Loss of weight (0-3)—Magnitude of weight loss in previous week
17) Insight (0-2)—Denial of illness While this invention has been particularly shown and described with references to example embodiments thereof, it will be understood by those skilled in the art that various changes in form and details may be made therein without departing from the scope of the invention encompassed by the appended claims.

What is claimed is:

1. A method of assessing a mental or physical condition of a subject, the method comprising in an automated system:
   inputting a speech waveform of the subject into the automated system;
   in the automated system, processing the speech waveform of the subject to locate occurrences of phones having symbols of a plurality of English phone symbols in the speech waveform;
   in the automated system, for each phone symbol of the plurality of phone symbols, extracting a value of at least one phone-specific prosodic or speech-excitation-source feature corresponding to said phone symbol from the occurrences of phones having said phone symbol located in the speech waveform of the subject;
   in the automated system, weighting the values of the extracted features corresponding to phone symbols with stored weights corresponding to said phone symbols to form values of a plurality of weighted extracted features and combining the values of the weighted extracted features to generate a combined measure that assesses the mental or physical condition of the subject, the stored weights derived from a correlation matrix representing correlations between the phone-specific features corresponding to the plurality of phone symbols and the mental or physical condition; and
   outputting an assessment of the condition using the generated combined measure.

2. The method of claim 1, wherein the condition has a measure and the correlations are between the measure and the phone-specific features corresponding to the phone symbols.

3. The method of claim 1, wherein the waveform speech of the subject is of running speech.

4. The method of claim 1, wherein the weighted extracted features correspond to a correlations dependent subset of the phone symbols.

5. The method of claim 1, wherein the condition is selected from traumatic brain injury, post-traumatic stress disorder, Parkinson's disease, Aphasia, Autism, Alzheimer's disease, stroke, sleep disorders, anxiety disorders, multiple sclerosis, cerebral palsy, and major depressive disorder (MDD).

6. The method of claim 2, wherein the condition is MDD and the measure is a Hamilton-D (HAMD) score or a subscore thereof.

7. The method of claim 1, wherein the at least one feature corresponding to each phone symbol extracted from the occurrences of phones with said phone symbol located in the speech waveform of the subject is selected from one or more of a duration, energy, pitch, aspiration, glottal flow or frequency-dependent energy feature.

8. The method of claim 1, wherein the at least one phone-specific features corresponding to each phone symbol extracted from the occurrences of phones with said phone symbol located in the speech waveform of the subject include durations of one or more phone symbols.

9. The method of claim 8, further including computing an average duration of occurrences of phones with a phone symbol in the speech waveform of the subject.

10. The method of claim 2, wherein:
    the phone-specific feature corresponding to the phone symbol is a phone-duration-based speech rate of the subject;
    the condition is MDD; and
    the measure is the psychomotor retardation sub-score of a Hamilton-D score.

11. The method of claim 1, wherein
    the condition is a Major Depressive Disorder and the measure is a Hamilton-D score or a sub score thereof;
    the phone-specific feature corresponding to the phone symbol extracted from the speech waveform of the subject is a duration of phones with the phone symbol;
    the method further includes computing average durations of phones corresponding to specific phone symbols in the speech waveform of the subject; and
    generating the assessment of the condition includes computing a weighted sum of the average durations of the specific phones, wherein the weights correspond to correlation coefficients between the average durations of the specific phones and the Hamilton-D score or a subscore thereof.

12. The method of claim 11, further including:
    generating an estimate of the Hamilton-D score of the subject or a sub score thereof; and
    displaying the estimate of the Hamilton-D score of the subject or a subscore thereof.

13. A method of assessing a mental or physical condition of a subject, the method comprising in an automated system:
    inputting a speech waveform of the subject into the automated system;
    in the automated system, recognizing occurrences of phones having symbols of a plurality of English phone symbols in the speech waveform of the subject;
    in the automated system, for each phone symbol of the plurality of phone symbols, extracting a value of at least one phone-specific feature corresponding to said phone symbol from the speech waveform of the subject having the mental or physical condition; and
    in the automated system, weighting values of extracted features corresponding to the plurality of phone symbols with stored weights to form values of a plurality of weighted extracted features and combining weighted extracted features to generate a combined measure that assesses a condition of the subject, the stored weights derived from a correlation matrix representing correlations between the one or more phone-specific features of a correlation-dependent subset of the phone symbols and the mental or physical condition; and outputting an assessment of the condition using the generated combined measure.

14. The method of claim 13, wherein the condition has a measure and the correlations are between the measure and the at least one phone-specific feature of the phone symbols.

15. The method of claim 13, wherein the condition is selected from traumatic brain injury, post-traumatic stress disorder, Parkinson's disease, Aphasia, Autism, Alzheimer's disease, stroke, sleep disorders, anxiety disorders, multiple sclerosis, cerebral palsy, and major depressive disorder (MDD).

16. The method of claim 14, wherein the condition is Major Depressive Disorder and the measure is a Hamilton-D score or a subscore thereof.

17. The method of claim 13, wherein the at least one phone-specific feature of the specific phone symbols are selected from one or more of duration, energy of specific phones, pitch of specific phones, aspiration of specific phones, glottal flow of specific phones or frequency-dependent energy of specific phone symbols.

18. The method of claim 13, wherein the at least one phone-specific feature of the phone symbols include duration of the specific phones in the speech waveform of the one or more subjects.

19. The method of claim 18, further including computing average duration of the one or more specific phones in the speech waveform of the subject.

20. The method of claim 14, wherein:
the condition is Major Depressive Disorder and the measure is a Hamilton-D score or a subscore thereof;
the phone-specific feature of the phones is the duration of the specific phones;
the method further includes computing average durations of the specific phones; and
the correlations are between the average durations of the specific phones and a Hamilton-D score or a subscore thereof.

21. An automated system for assessing a mental or physical condition of a subject, the system comprising:
an input of a speech waveform of the subject;
a phone recognizer that recognizes occurrences of phones having symbols of a plurality of English phone symbols in the speech waveform of the subject;
a feature extractor that extracts, for each phone symbol of the plurality of phone symbols, a value of at least one phone-specific prosodic or speech-excitation-source feature corresponding to said phone symbol from the occurrences of phones having said phone symbol located in the speech waveform of the subject; and
an assessment generator that weights values of the extracted features corresponding to the plurality of phone symbols with stored weights corresponding to said phone symbols to form a plurality of weighted extracted features and combines weighted extracted features of plural specific phones to generate a combined measure that assesses the mental or physical condition in the subject, the stored weights derived from a correlation matrix representing correlations between the one or more phone-specific features, of the specific phones extracted from the speech waveform of the subject, and the mental or physical condition; and
a display for outputting an assessment of the condition using the generated combined measure.

22. The system of claim 21, wherein the condition has a measure and the correlation is between the measure and the phone-specific features corresponding to the phone symbols.

23. The system of claim 21, wherein the speech waveform of the subject is of running speech.

24. The system of claim 21, wherein the weighted extracted features correspond to a correlations dependent subset of the phone symbols.

25. The system of claim 21, wherein the condition is selected from traumatic brain injury, post-traumatic stress disorder, Parkinson's disease, Aphasia, Autism, Alzheimer's disease, stroke, sleep disorders, anxiety disorders, multiple sclerosis, cerebral palsy, and major depressive disorder (MDD).

26. The system of claim 22, wherein the condition is MDD and the measure is a Hamilton-D (HAMD) score or a subscore thereof.

27. The system of claim 21, wherein the feature extractor extracts one or more of duration of specific phones, energy of specific phones, pitch of specific phones, aspiration of phones, glottal flow of specific phones or frequency-dependent energy of specific phone symbols.

28. The system of claim 21, wherein the feature extractor extracts durations of one or more phone symbols.

29. The system of claim 23, wherein the feature extractor further computes an average duration of the phones with a phone symbol in the speech waveform of the subject.

30. The system of claim 21, wherein:
the phone-specific feature corresponding to the phone symbol is a phone-duration-based speech rate of the subject;
the condition is MDD; and
the measure is the psychomotor retardation sub-score of a Hamilton-D score.

31. The system of claim 21, wherein
the condition is Major Depressive Disorder and the measure is a Hamilton-D score or a subscore thereof;
the feature extractor extracts the durations corresponding to the phone symbol and further computes average durations of phones with the phone symbol in the speech waveform of the subject; and
the assessment generator computes a weighted sum of the average durations of the phone symbols, wherein the weights correspond to correlation coefficients between the average durations of the specific phones and the Hamilton-D score or a subscore thereof.

32. The system of claim 31, wherein:
the assessment generator further generates an estimate of the Hamilton-D score of the subject or a subscore thereof; and
the display displays the estimate of the Hamilton-D score of the subject or a subscore thereof.

33. An automated system for assessing a mental or physical condition of a subject, the system comprising:
an input of a speech waveform from the subject;
a phone recognizer that recognizes occurrences of phones having symbols of a plurality of English phone symbols in the speech waveform of the subject;
a feature extractor that extracts, for each phone symbol of the plurality of phone symbols, a value of at least one or more phone-specific prosodic or speech-excitation-source feature corresponding to said phone symbol from the occurrences of phones having said phone symbol located in the speech waveform of the subject;
an assessment generator that weights values of extracted features with stored weights corresponding to said phone symbols to form a plurality of weighted extracted features and combines weighted extracted features of plural phone symbols to generate a combined measure that assesses the mental or physical condition in the subject, the stored weights derived from a correlation matrix representing correlations between the one or more phone-specific features of a correlation-dependent subset of the specific phones extracted from the speech waveform of the subject and the mental or physical condition; and a display for outputting an assessment of the condition using the generated combined measure.

34. The method of claim 1, further comprising monitoring the condition based on the combined measure.

35. The method of claim 13, further comprising monitoring the condition based on the combined measure.

\* \* \* \* \*